(12) United States Patent
Waite, II et al.

(10) Patent No.: US 8,939,986 B2
(45) Date of Patent: Jan. 27, 2015

(54) SURGICAL INSTRUMENTS FOR USE IN SURGICALLY PREPARING A TIBIA FOR IMPLANTATION OF A PROSTHETIC COMPONENT

(75) Inventors: David W. Waite, II, Winona Lake, IN (US); Scott M. Thomas, Fort Wayne, IN (US); Duncan G. Young, Hebden Bridge West (GB); Matthew S. Wallace, Huntertown, IN (US); Duncan J. Beedall, Leeds (GB)

(73) Assignee: DePuy (Ireland) (IE)

( * ) Notice: Subject to any disclaimer, the term of this patent is extended or adjusted under 35 U.S.C. 154(b) by 63 days.

(21) Appl. No.: 13/530,934

(22) Filed: Jun. 22, 2012

(65) Prior Publication Data
US 2013/0006377 A1 Jan. 3, 2013

Related U.S. Application Data

(60) Provisional application No. 61/503,245, filed on Jun. 30, 2011.

(51) Int. Cl.
| | | |
|---|---|---|
| A61B 17/58 | (2006.01) | |
| A61B 17/60 | (2006.01) | |
| A61F 2/00 | (2006.01) | |
| A61F 2/46 | (2006.01) | |
| A61B 17/17 | (2006.01) | |
| A61F 2/38 | (2006.01) | |
| A61B 17/16 | (2006.01) | |

(52) U.S. Cl.
CPC ............... *A61F 2/4684* (2013.01); *A61F 2/389* (2013.01); *A61B 17/1675* (2013.01); *A61B 17/1764* (2013.01)

USPC .................................................. 606/96; 606/88

(58) Field of Classification Search
USPC ........................................ 606/87, 88, 96, 104
See application file for complete search history.

(56) References Cited

U.S. PATENT DOCUMENTS

| D269,547 S | 6/1983 | Rosenthal |
|---|---|---|
| 4,659,331 A | 4/1987 | Matthews et al. |
| D338,270 S | 8/1993 | Stephens et al. |
| 5,306,276 A | 4/1994 | Johnson et al. |
| 5,356,414 A | 10/1994 | Cohen et al. |
| 5,364,401 A | 11/1994 | Ferrante et al. |
| 5,486,178 A | 1/1996 | Hodge |
| 5,514,143 A | 5/1996 | Bonutti et al. |
| 5,540,696 A | 7/1996 | Booth et al. |

(Continued)

FOREIGN PATENT DOCUMENTS

| EP | 1219269 A1 | 7/2002 |
|---|---|---|
| EP | 1415625 A2 | 3/2004 |

(Continued)

OTHER PUBLICATIONS

European Search Report for European Application No. 12174178.9-2310, Sep. 6, 2012, 6 pages.

(Continued)

*Primary Examiner* — Andrew Yang
(74) *Attorney, Agent, or Firm* — Barnes & Thornburg LLP

(57) ABSTRACT

Orthopaedic surgical instruments including a base trial adapted to be positioned on a proximal end of a patient's resected tibia, and a guide tower including a tower base adapted to be positioned on the base trial. A method of use is also described.

20 Claims, 25 Drawing Sheets

(56) References Cited

U.S. PATENT DOCUMENTS

| | | | |
|---|---|---|---|
| 5,569,260 A | 10/1996 | Petersen | |
| 5,597,379 A | 1/1997 | Haines et al. | |
| 5,601,565 A | 2/1997 | Huebner | |
| 5,611,802 A | 3/1997 | Samuelson et al. | |
| 5,643,272 A | 7/1997 | Haines et al. | |
| 5,649,928 A | 7/1997 | Grundei | |
| 5,683,469 A | 11/1997 | Johnson et al. | |
| 5,690,636 A | 11/1997 | Wildgoose et al. | |
| 5,702,464 A | 12/1997 | Lackey et al. | |
| 5,704,941 A | 1/1998 | Jacober et al. | |
| 5,709,689 A | 1/1998 | Ferrante et al. | |
| 5,720,752 A | 2/1998 | Elliott et al. | |
| 5,735,904 A | 4/1998 | Pappas | |
| 5,749,876 A | 5/1998 | Duvillier et al. | |
| 5,769,854 A | 6/1998 | Bastian et al. | |
| 5,788,700 A | 8/1998 | Morawa et al. | |
| 5,860,980 A | 1/1999 | Axelson, Jr. et al. | |
| 5,935,128 A | 8/1999 | Carter et al. | |
| 5,976,147 A | 11/1999 | Lasalle et al. | |
| 5,989,261 A | 11/1999 | Walker et al. | |
| 6,022,377 A | 2/2000 | Nuelle et al. | |
| 6,024,746 A | 2/2000 | Katz et al. | |
| 6,102,955 A | 8/2000 | Mendes et al. | |
| 6,159,216 A * | 12/2000 | Burkinshaw et al. | 606/88 |
| 6,344,043 B1 | 2/2002 | Pappas | |
| 6,355,045 B1 | 3/2002 | Gundlapalli et al. | |
| 6,478,799 B1 | 11/2002 | Williamson | |
| 6,485,521 B1 | 11/2002 | Say et al. | |
| 6,712,824 B2 | 3/2004 | Millard et al. | |
| 6,821,470 B2 | 11/2004 | Gundlapalli et al. | |
| 6,942,670 B2 * | 9/2005 | Heldreth et al. | 606/102 |
| D518,178 S | 3/2006 | Christiansen | |
| 7,104,996 B2 | 9/2006 | Bonutti | |
| 7,291,174 B2 | 11/2007 | German et al. | |
| 7,344,541 B2 | 3/2008 | Haines et al. | |
| 7,695,519 B2 | 4/2010 | Collazo | |
| D619,251 S | 7/2010 | Justiniano-Garcia et al. | |
| D666,713 S | 9/2012 | Waite et al. | |
| 2004/0039450 A1 | 2/2004 | Griner et al. | |
| 2005/0075640 A1 | 4/2005 | Collazo et al. | |
| 2006/0089641 A1 | 4/2006 | Collazo | |
| 2006/0184176 A1 | 8/2006 | Straszheim-Morley et al. | |
| 2007/0233137 A1 | 10/2007 | Seo et al. | |
| 2008/0119938 A1 | 5/2008 | Oh | |
| 2008/0147075 A1 | 6/2008 | Bonutti | |
| 2008/0154270 A1 | 6/2008 | Haines et al. | |
| 2008/0221569 A1 | 9/2008 | Moore et al. | |
| 2008/0269901 A1 | 10/2008 | Baynham et al. | |
| 2009/0076514 A1 | 3/2009 | Haines | |
| 2009/0082773 A1 | 3/2009 | Haines | |
| 2009/0125114 A1 | 5/2009 | May et al. | |
| 2009/0138018 A1 | 5/2009 | Haines | |
| 2010/0016979 A1 | 1/2010 | Wyss et al. | |
| 2010/0076438 A1 | 3/2010 | Correia et al. | |
| 2010/0082111 A1 | 4/2010 | Thomas | |
| 2010/0125337 A1 | 5/2010 | Grecco et al. | |
| 2010/0298941 A1 | 11/2010 | Hes et al. | |
| 2011/0066246 A1 | 3/2011 | Ries et al. | |
| 2011/0178605 A1 | 7/2011 | Auger et al. | |
| 2012/0041566 A1 | 2/2012 | Lenz et al. | |
| 2012/0323334 A1 | 12/2012 | Jones et al. | |
| 2013/0006252 A1 | 1/2013 | Waite, II et al. | |
| 2013/0006253 A1 | 1/2013 | Waite, II et al. | |
| 2013/0006370 A1 | 1/2013 | Wogoman et al. | |
| 2013/0006371 A1 | 1/2013 | Wogoman et al. | |
| 2013/0006376 A1 | 1/2013 | Wogoman et al. | |

FOREIGN PATENT DOCUMENTS

| | | |
|---|---|---|
| EP | 1836997 A1 | 9/2007 |
| EP | 2168537 A1 | 3/2010 |
| WO | 9925263 A1 | 3/1999 |
| WO | 0013597 A1 | 3/2000 |
| WO | 2008054389 A1 | 5/2008 |
| WO | 2011073632 A1 | 6/2011 |

OTHER PUBLICATIONS

European Search Report for European Application No. 12174174.8-2310, Nov. 9, 2012, 11 pages.

Zimmer NexGen LCCK, Surgical Technique for use with LCCK 4-in-1 Instrument, 2009, 52 pages.

DePuy Orthopaedics, Inc., Sigma Revision and M.B.T. Revision Tray, Surgical Technique, 2008, 82 pages.

Smith & Nephew, Legion, Revision Knee System, Surgical Technique, 2005, 40 pages.

Biomet, Vanguard SSK, Revision System, Surgical Technique, Feb. 2008, 64 pages.

Gmk Revision, Surgical Technique, Ref. 99.27.12US rev. 1, 1999, 74 pages.

PFC Sigma RP-F, Specialist 2 Instruments, Surgical Technique, Performance in Flexion, 2007, 32 pages.

P.F.C. Sigma Rotating Platform Knee System with M.B.T Tray, Primary Procedure with a Curved or Posterior Stablised Implant, 2003, 43 pages.

LCS High Performance Instruments, Surgical Technique, 2008, 44 pages.

Sigma High Performance Instruments, Design Rationale, 2007, 12 pages.

Sigma High Performance Instruments, Classic Surgical Technique, 2010, 52 pages.

Coordinate Ultra Revision Knee System, Surgical Technique, 1997, p. 24.

P.F.C. Sigma Knee System, Revision, Surgical Technique, 2000, p. 66.

Sigma Revision and M.B.T. Revision Tray, Surgical Technique, 2012, p. 84.

S-Rom Noiles Rotating Hinge, Surgical Technique, 2012, p. 76.

European Search Report, European Application No. 13175055.6-1654, Sep. 16, 2013, 5 pages.

Declaration of Thomas E. Wogoman (with Exhibits A-I), executed Aug. 11, 2014, 145 pages.

* cited by examiner

SURGICAL INSTRUMENTS FOR USE IN SURGICALLY PREPARING A TIBIA FOR IMPLANTATION OF A PROSTHETIC COMPONENT

This application claims priority under 35 U.S.C. §119 to U.S. Patent Application No. 61/503,245, which was filed on Jun. 30, 2011 and is incorporated herein by reference.

CROSS-REFERENCE

Cross-reference is made to U.S. Provisional Patent Application Ser. No. 61/503,331 entitled "METHOD OF SURGICALLY PREPARING A TIBIA FOR IMPLANTATION OF A PROSTHETIC COMPONENT" by David Waite et al.; U.S. Provisional Patent Application Ser. No. 61/503,324 entitled "SURGICAL INSTRUMENT ASSEMBLIES FOR USE IN SURGICALLY PREPARING A TIBIA FOR IMPLANTATION OF A PROSTHETIC COMPONENT" by David Waite et al.; and U.S. Design patent application Ser. No. 29/396,478 entitled "KEEL PUNCH" by David Waite et al., each of which is assigned to the same assignee as the present application and each of which is hereby incorporated by reference.

TECHNICAL FIELD

The present disclosure relates generally to orthopaedic surgical instruments and, more particularly, to surgical instruments used with a patient's tibia.

BACKGROUND

Joint arthroplasty is a well-known surgical procedure by which a diseased and/or damaged natural joint is replaced by a prosthetic joint. A typical knee prosthesis includes a tibial tray, a femoral component, and a tibial bearing positioned between the tibial tray and the femoral component. The tibial tray typically includes a plate having a stem extending distally therefrom. The stem is implanted in a prepared medullary canal of the patient's tibia. Once implanted in such a manner, the tibial tray provides a surface on the proximal end of the tibia to which the tibial bearing may be affixed.

To facilitate the replacement of the natural joint with the knee prosthesis, orthopaedic surgeons use a variety of orthopaedic surgical instruments such as, for example, tibial trials, drill guides, and other surgical instruments.

SUMMARY

According to one aspect, a method of surgically preparing a proximal end of a patient's tibia is disclosed. The method includes positioning a base trial on a resected surface of the proximal end of the patient's tibia, the base trial having an opening defined therein, placing a guide tower on the base trial positioned on the resected surface selecting a keel punch for insertion into the patient's tibia, and securing the keel punch to a lower end of a handle by engaging a lever of the handle with the keel punch. The method also includes inserting the keel punch and the lower end of the handle through an upper end of the guide tower, impacting the keel punch into the proximal end of the patient's tibia through the opening of the base trial, and contacting an inner surface of the guide tower with the lever to disengage the lever from the keel punch. The method further includes moving the lower end of the handle toward the upper end of the guide tower after impacting the keel punch, engaging the lever with the guide tower to secure the handle to the guide tower, and using the handle to remove the guide tower from the base trial.

In some embodiments, contacting the inner surface of the guide tower may include contacting an upper arm of the lever to the inner surface of the guide tower to actuate the lever, and engaging the lever with the guide tower to secure the handle to the guide tower may include moving the upper arm from contact with the inner surface of the guide tower. In some embodiments, securing the keel punch to the lower end of the handle may include engaging a first flange of the lever with the keel punch. Additionally, in some embodiments, engaging the lever with the guide tower may include engaging a second flange of the lever with the guide tower.

In some embodiments, the method may also include inserting a surgical drill into the base trial and the guide tower to ream the patient's tibia. In some embodiments, inserting the surgical drill may include advancing the surgical drill into the proximal end of the patient's tibia until a first horizontal line of a plurality of horizontal lines defined on the surgical drill is substantially aligned with the upper end of the guide tower.

In some embodiments, the method may include attaching a drill stop to the guide tower. Additionally, in some embodiments, inserting the surgical drill into the base trial and the guide tower may include advancing the surgical drill through the drill stop until a first horizontal line of a plurality of horizontal lines is substantially aligned with an upper end of the drill stop. In some embodiments, placing the guide tower on the base trial may include inserting a pair of fixation pins extending from the guide tower into the proximal end of the patient's tibia.

In some embodiments, the method may include attaching a second handle to the base trial prior to positioning the base trial on the resected surface.

According to another aspect, the method of surgically preparing a proximal end of a patient's resected tibia includes selecting a keel punch for insertion into the patient's resected tibia, securing a handle to the keel punch by actuating a lever of the handle to engage the lever with the keel punch, and impacting the keel punch into the patient's resected tibia. The lever of the handle is automatically actuated while the keel punch is being impacted into the patient's resected tibia such that the lever is disengaged from the keel punch.

In some embodiments, the method may include positioning the keel punch over a lower end of the handle prior to actuating the lever of the handle. In some embodiments, the method may include inserting the keel punch and the lower end of the handle into an upper end of a guide tower.

In some embodiments, inserting the keel punch and the lower end of the handle into the guide tower may include placing an upper arm of the lever into contact with an inner surface of the guide tower to disengage the lever from the keel punch. In some embodiments, the method may include moving the lower end of the handle toward the upper end of the guide tower after impacting the keel punch into the patient's resected tibia to move the upper arm of the lever from contact with the inner surface of the guide tower.

Additionally, in some embodiments, the method may include moving the lower end of the handle toward the upper end of the guide tower after impacting the keel punch into the patient's resected tibia, and engaging the lever with the guide tower to secure the handle to the guide tower. The method may include positioning a base trial on a resected surface of the proximal end of the patient's resected tibia, the base trial having an opening defined therein, and placing the guide tower on the base trial before inserting the keel punch and the lower end of the handle into the guide tower.

According to another aspect, the method of surgically preparing a proximal end of a patient's tibia includes positioning a base trial on a resected surface of the proximal end of the patient's tibia, the base trial having an opening and a pair of fixation pin holes defined therein, positioning a guide tower over the base trial, inserting a pair of fixation pins extending from the guide tower through the pair of fixation pin holes of the base trial and into the proximal end of the patient's tibia, placing the guide tower on the base trial, and inserting a surgical drill into the base trial and the guide tower to ream the patient's tibia. In some embodiments, inserting the surgical drill into the base trial may include advancing the surgical drill into the proximal end of the patient's tibia until a first horizontal line of a plurality of horizontal lines defined on the surgical drill is substantially aligned with an upper end of the guide tower. In some embodiments, the method may include attaching a drill stop to the guide tower. Additionally, in some embodiments, inserting the surgical drill may include advancing the surgical drill into the proximal end of the patient's tibia until a first horizontal line of a plurality of horizontal lines is substantially aligned with an upper end of the drill stop.

In some embodiments, the method may include selecting a keel punch for insertion into the patient's tibia, securing a handle to the keel punch by engaging a lever of the handle with the keel punch, and impacting the keel punch into the patient's tibia. The lever may be automatically actuated while the keel punch is being impacted into the patient's tibia such that the lever is disengaged from the keel punch.

According to another aspect, an orthopaedic surgical instrument assembly is disclosed. The orthopaedic surgical instrument assembly includes a base trial adapted to be positioned on a proximal end of a patient's resected tibia, and a guide tower. The base trial includes a plate having an opening defined therein, and a pair of fixation pin holes defined in an anterior aspect. The guide tower includes a tower base adapted to be positioned on the base trial and a pair of fixation pins extending downwardly from an anterior aspect of the tower base. The tower base has a passageway defined therein that is configured to be substantially aligned with the opening of the plate when the tower base is positioned on the base trial. Each of the fixation pins is sized to be received in, and extend outwardly from, each of the fixation pin holes of the base trial when the tower base is positioned on the base trial.

In some embodiments, the assembly may include a second pair of fixation pins. The plate of the base trial may have a second pair of fixation pin holes defined in the anterior aspect and each of the second pair of fixation pins is sized to be received in, and extend outwardly from, each of the second pair of fixation pin holes.

In some embodiments, the assembly may include a handle removably coupled to the anterior aspect of the plate. In some embodiments, the plate may have a notch defined therein and a pair of apertures defined on each side of the notch. Additionally, in some embodiments, the handle may include a body, a pair of tabs extending from the body that are sized to be received in the pair of apertures, and a lever arm pivotally coupled to the body. The lever arm may have a flange and may be movable between a first position in which the flange is received in the notch defined in the plate such that the handle is secured to the base trial, and a second position in which the flange is spaced apart from the notch such that the handle may be removed from the base trial.

In some embodiments, the assembly may include a biasing member that biases the lever arm in the first position. In some embodiments, the opening of the base trial and the passageway of the guide tower may be sized to receive a surgical drill.

Additionally, in some embodiments, the assembly may include a drill stop adapted to be positioned at an upper end of the guide tower. In some embodiments, the drill stop may be formed from a first material and the guide tower may be formed from a second material different from the first material.

In some embodiments, the plate may have a plurality of alignment etchings defined in the anterior aspect to align the plate with the proximal end of the patient's resected tibia.

According to another aspect, the orthopaedic surgical instrument assembly includes a base trial adapted to be positioned on a proximal end of a patient's resected tibia and a guide tower. The base trial includes a plate having an opening defined therein. The guide tower includes a tower base adapted to be positioned on the base trial. The tower base has an anterior surface, an inner surface defining a passageway that is configured to be substantially aligned with the opening of the plate when the tower base is positioned on the base trial, a first aperture extending inwardly from the anterior surface to the inner surface such that the first aperture is in communication with the passageway, and a second aperture extending inwardly from the anterior surface to the inner surface such that the second aperture is in communication with the passageway. The second aperture is positioned above the first aperture.

In some embodiments, the plate may have a plurality of fixation pin holes defined in an anterior aspect thereof. In some embodiments, the tower base of the guide tower may include a pair of fixation pins extending downwardly from an anterior aspect of the tower base. Each of the fixation pins may be sized to be received in, and extend outwardly from, one of the fixation pin holes of the base trial when the tower base is positioned on the base trial.

In some embodiments, the assembly may include a surgical drill, and the opening of the base trial and the passageway of the guide tower may be sized to receive the surgical drill. Additionally, in some embodiments, the surgical drill may have a plurality of horizontal lines defined thereon. The guide tower may extend a predetermined height corresponding to a first horizontal line of the plurality of horizontal lines and a first predetermined drilled-hole depth in the patient's tibia. In some embodiments, the assembly may further include a drill stop adapted to be positioned at an upper end of the guide tower. The drill stop and the guide tower may extend a second predetermined height corresponding to a second horizontal line of the plurality of horizontal lines and a second predetermined drilled-hole depth in the patient's tibia.

According to another aspect, the orthopaedic surgical instrument assembly includes a guide tower for a surgical drill, and the guide tower includes a tower base and a pair of fixation pins extending downwardly from the anterior aspect of the tower base. The tower base has an anterior aspect having an anterior surface, an inner surface defining a vertically-extending passageway, a first aperture, the first aperture extending orthogonally relative to the passageway from the anterior surface to the inner surface such that the first aperture is in communication with the passageway, and a second aperture positioned above the first aperture, the second aperture extending orthogonally relative to the passageway from the anterior surface to the inner surface such that the second aperture is in communication with the passageway. Each fixation pin is configured to be inserted into a proximal end of a patient's resected tibia.

In some embodiments, the inner surface may define a circular opening in an upper end of the tower base and the passageway may extend downwardly from the circular opening. In some embodiments, the inner surface may define a pair of slots connected to the circular opening. In some embodiments, the assembly may include a drill stop adapted to be positioned at an upper end of the guide tower. Additionally, in some embodiments, each fixation pin of the pair of fixation pins may include a first section having a first cross-sectional diameter and a second section extending downwardly from the first section that has a second cross-sectional diameter. The second cross-sectional diameter is less than the first cross-sectional diameter.

According to another aspect, the orthopaedic surgical instrument assembly includes a handle, a keel punch configured to be inserted into a proximal end of a surgically-prepared tibia of a patient, and a guide tower. The handle includes an elongated body and a lever pivotally coupled to the body at a joint. The lever includes a first flange positioned below the joint, the first flange extending in a first direction, and a second flange positioned above the joint such that the joint is positioned between the first flange and the second flange. The second flange extends in a second direction opposite the first direction. The keel punch includes a lip configured to be engaged by the first flange of the lever. The guide tower includes a tower base having an inner surface that defines a passageway sized to receive the keel punch and the body of the handle. The guide tower also includes an inner wall that defines a rectangular aperture in the tower base. The inner wall is configured to be engaged by the second flange of the lever.

In some embodiments, the handle may include a guide pin extending from the body, and the keel punch may include a post having an opening defined therein sized to receive the guide pin. The lip of the keel punch may extend outwardly from the post.

In some embodiments, the lever may be configured to pivot relative to the body of the handle between a plurality of lever positions. The plurality of lever positions may include a first lever position in which the first flange is engaged with the lip of the keel punch and a second lever position in which the first flange is disengaged from the lip of the keel punch. Additionally, in some embodiments, the handle may be moveable within the passageway of the guide tower between a plurality of handle positions, and the lever may include an upper arm configured to contact the inner surface of the tower base and thereby pivot the lever relative to the body of the handle when the handle is positioned in at least one of the handle positions.

In some embodiments, the plurality of handle positions may include a first handle position in which the upper arm is spaced apart from the inner surface of the tower base such that the lever is positioned in the first lever position. In some embodiments, the plurality of handle positions may include a second handle position in which the upper arm is in contact with the inner surface of the tower base such that the lever is positioned in the second lever position.

In some embodiments, the second flange of the lever may be engaged with the inner wall of the guide tower when the handle is in the first handle position. Additionally, in some embodiments, the second flange of the lever may be disengaged from the inner wall of the guide tower when the handle is in the second handle position. In some embodiments, the lever may be configured to be in the second lever position when a predetermined amount of force is applied to the upper arm.

In some embodiments, the handle may include a biasing element that biases the lever in the first lever position, and the predetermined amount of force required to place the lever in the second lever position may be greater than the bias of the biasing element. In some embodiments, the biasing element may be a metal spring.

In some embodiments, the assembly may include a base trial adapted to be positioned on the proximal end of a patient's resected tibia. The base trial may have an opening defined therein sized to receive a lower end of the keel punch. The tower base may be adapted to be positioned on the base trial such that the passageway of the tower base is substantially aligned with the opening.

According to another aspect, the orthopaedic surgical instrument assembly includes a handle including a body having a lower end, a guide pin extending from the lower end, and a lever pivotally coupled to the body. The lever includes a flange positioned below the lower end of the body, and the flange extends inwardly toward the guide pin. The assembly also includes a keel punch configured to be inserted into a proximal end of a surgically-prepared tibia of a patient. The keel punch includes a post having an opening defined therein sized to receive the guide pin, and a lip extending outwardly from the post. The lip is configured to be engaged by the flange of the lever. The lever is configured to pivot relative to the body of the handle between a plurality of lever positions. The plurality of lever positions includes a first lever position in which the flange is engaged with the lip of the keel punch and a second lever position in which the flange is disengaged from the lip of the keel punch.

In some embodiments, the handle may include a biasing element that biases the lever in the first lever position. In some embodiments, the keel punch further includes a main platform and a pair of arms extending outwardly from the main platform, and the post of the keel punch extends from the main platform above the pair of arms. Additionally, in some embodiments, the keel punch has a plurality of downwardly-facing teeth defined therein.

According to another aspect, the orthopaedic surgical instrument assembly includes a handle. The handle includes an elongated body and a lever pivotally coupled to the body at a joint positioned at an end of the elongated body. The lever includes a first flange positioned below the joint, and the first flange extends in a first direction. The lever also includes a second flange positioned above the joint such that the joint is positioned between the first flange and the second flange. The second flange extends in a second direction opposite the first direction.

In some embodiments, the elongated body includes a grip. Additionally, in some embodiments, the assembly may include a keel punch configured to be inserted into a proximal end of a surgically-prepared tibia of a patient. The keel punch may include a post having an opening defined therein and a lip extending from the post.

In some embodiments, the handle may include a guide pin extending from the body. The guide pin may be received in the opening of the keel punch, and the first flange of the lever may be engaged with the lip of the keel punch.

In some embodiments, the assembly may further include a guide tower. The guide tower may include a tower base having an inner surface that defines the passageway that receives the body of the handle, and an inner wall defining an aperture in the inner surface of the tower base. The second flange of the lever may be engaged with the inner wall of the guide tower.

BRIEF DESCRIPTION OF THE DRAWINGS

The detailed description particularly refers to the following figures, in which.

DETAILED DESCRIPTION OF THE DRAWINGS

Figure 1:
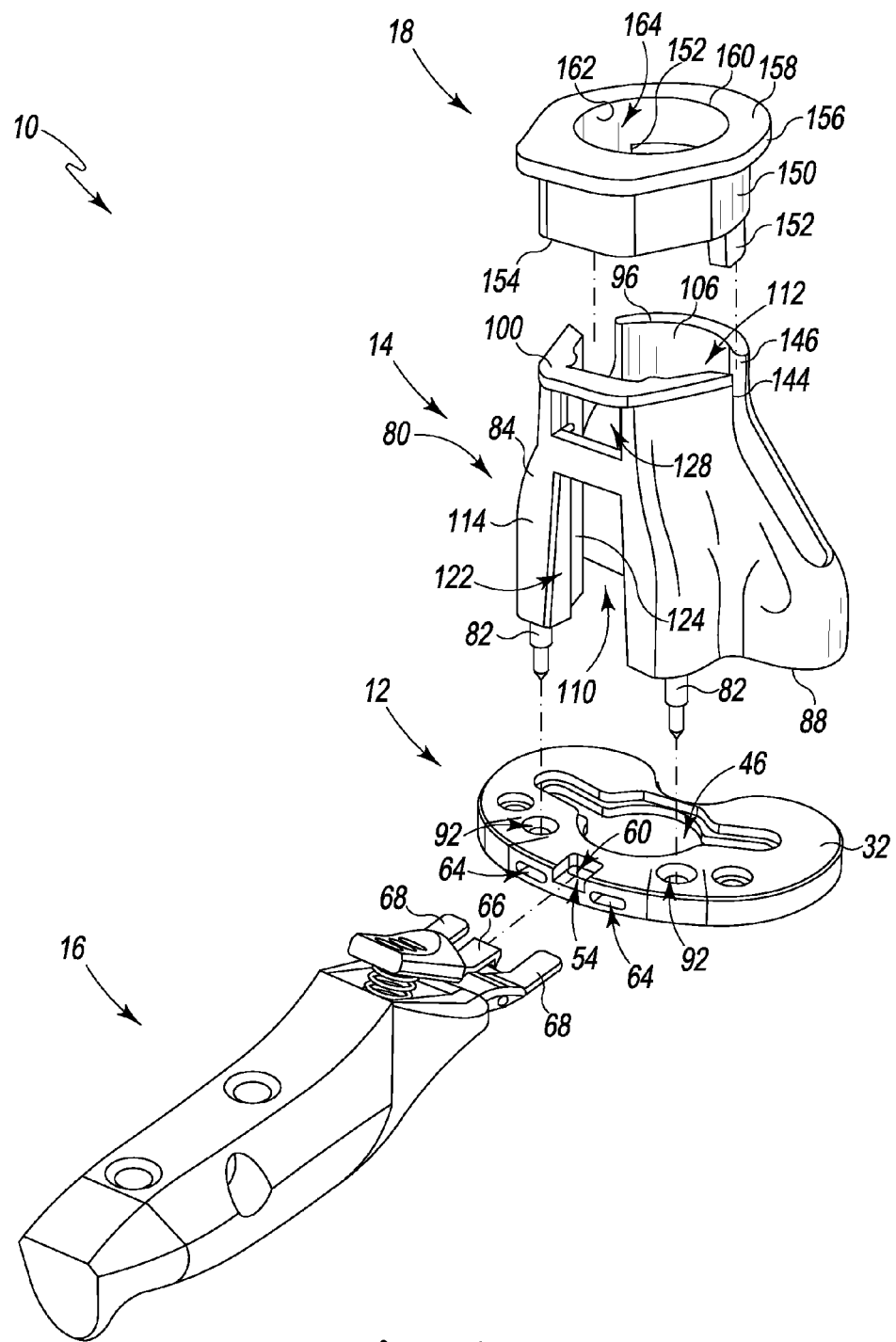
FIG. 1 is an exploded, perspective view of an orthopaedic surgical instrument assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIGS. 1-10, an orthopaedic surgical instrument assembly 10 (hereinafter assembly 10) for use during joint arthroplasty procedures, such as a total knee replacement procedure, is shown. It should be appreciated that although the assembly 10 is described below in regard to the performance of a total knee replacement procedure, certain concepts associated with the assembly 10 may be utilized in replacement procedures of numerous other joints throughout the body. As shown in FIG. 1, the assembly 10 includes a tibial base trial 12, a guide tower 14, a detachable alignment handle 16, and a drill stop 18.

In operation, the orthopaedic surgical instrument assembly 10 may be utilized to surgically prepare a proximal end 20 of a patient's resected tibia 22 (see FIG. 26) for implantation of a tibial prosthetic component, such as a tibial tray, during the performance of an orthopaedic surgical procedure. The tibial base trial 12 and the guide tower 14 are positioned on the resected surface 400 of the proximal end 20 of the patient's tibia 22, and the surgeon uses the trial 12 and the tower 14 to guide, for example, a surgical drill while reaming the proximal end 20 of the patient's tibia 22. Thereafter, a keel punch 220 (see FIG. 7) is impacted into the proximal end 20 of the patient's tibia 22 before the guide tower 14 is removed.

Figure 2:
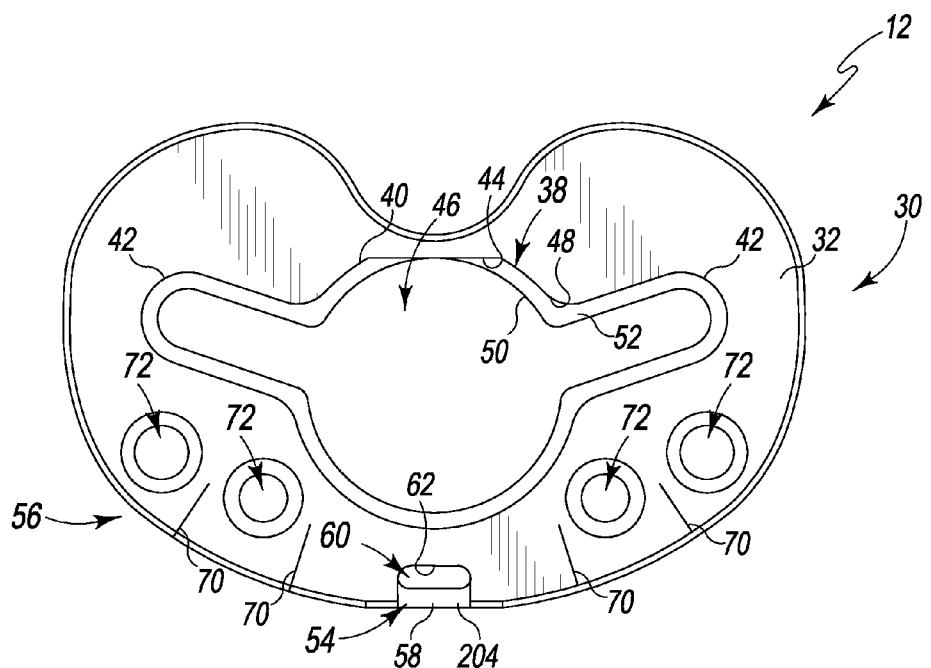
FIG. 2 is a top plan view of a tibial base trial of the orthopaedic surgical assembly of FIG. 1.
Figure 3:
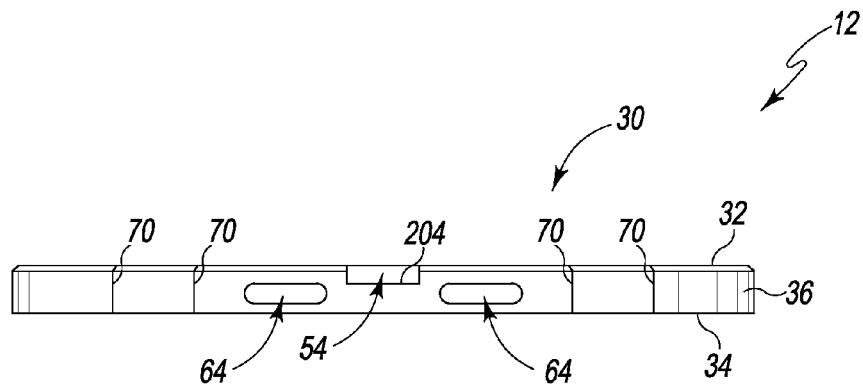
FIG. 3 is an anterior side elevation view of the tibial base trial of FIG. 2.

Referring now to FIGS. 1-3, the base trial 12 includes a plate 30 having an upper surface 32, a lower surface 34, and an outer sidewall 36 extending between the surfaces 32, 34. The plate 30 has a plate opening 38 defined in the upper surface 32. As shown in FIG. 2, the plate opening 38 has a central opening 40 and a pair of elongated openings 42 extending outwardly therefrom. An inner wall 44 extends downwardly from the opening 38 to define a passageway 46 through the plate 30. The inner wall 44 includes an upper wall 48 and a lower wall 50 offset or otherwise spaced inwardly from the upper wall 48. The upper wall 48 and lower wall 50 cooperate to define a shelf surface 52 therebetween. As will be discussed in greater detail below, the configuration of the passageway 46 permits the advancement of various surgical drills, punches, and other instruments into the proximal end 20 of the patient's resected tibia 22.

The plate 30 also includes a lever-receiving notch 54 defined in an anterior aspect 56 thereof. The notch 54 includes a channel 58 that is defined in the upper surface 32 and extends posteriorly from the outer sidewall 36. An oblong-shaped slot 60 is defined in the posterior end 62 of the channel 58. The slot 60 extends downwardly through the lower surface 34 of the plate 30. As shown in FIG. 3, a pair of oblong-shaped apertures 64 is defined in the sidewall 36, one on each side of the notch 54. As will be discussed in greater detail below, the notch 54 and the apertures 64 are configured to receive a lever 66 and a pair of pins 68, respectively, associated with the alignment handle 16.

A plurality of alignment etchings 70 extend along the upper surface 32 and the outer sidewall 36 of the plate 30. The surgeon may use one or more of the alignment etchings 70 to properly position the base trial 12 on the proximal end 20 of the patient's resected tibia 22. The plate 30 also includes a number of fastener holes 72 that are defined in the anterior aspect 56 thereof. The fastener holes 72 are configured to receive fasteners such as, for example, fixation pins 74 (see FIG. 13), which may be utilized to secure the base trial 12 to the proximal end 20 of the patient's resected tibia 22

Figure 4:
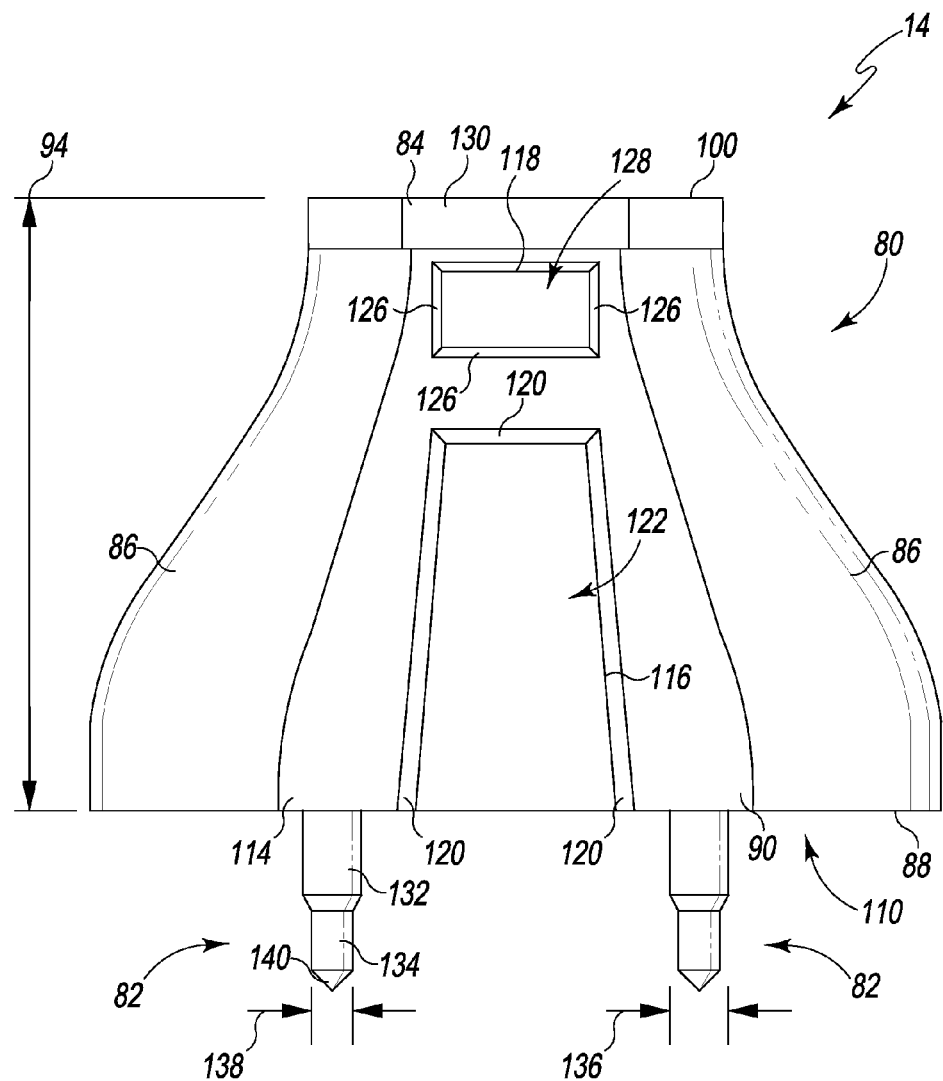
FIG. 4 is an anterior side elevation view of a guide tower of the orthopaedic surgical assembly of FIG. 1.

As described above, the assembly 10 also includes the guide tower 14, which is configured to be positioned on the plate 30 during use. As shown in FIG. 4, the guide tower 14 includes a tower base 80 and a pair of fixation pins 82 extending downwardly from the tower base 80. The tower base 80 includes a main body 84 and a pair of arms 86 extending outwardly from the main body 84. A bottom surface 88 of the tower base 80 is configured to be positioned on the upper surface 32 of the plate 30, and the fixation pins 82 extend downwardly from the anterior aspect 90 of the bottom surface 88. The main body 84 has a height 94, which may correspond to a predetermined drilling depth in the patient's tibia 22, as described in greater detail below.

Figure 5:
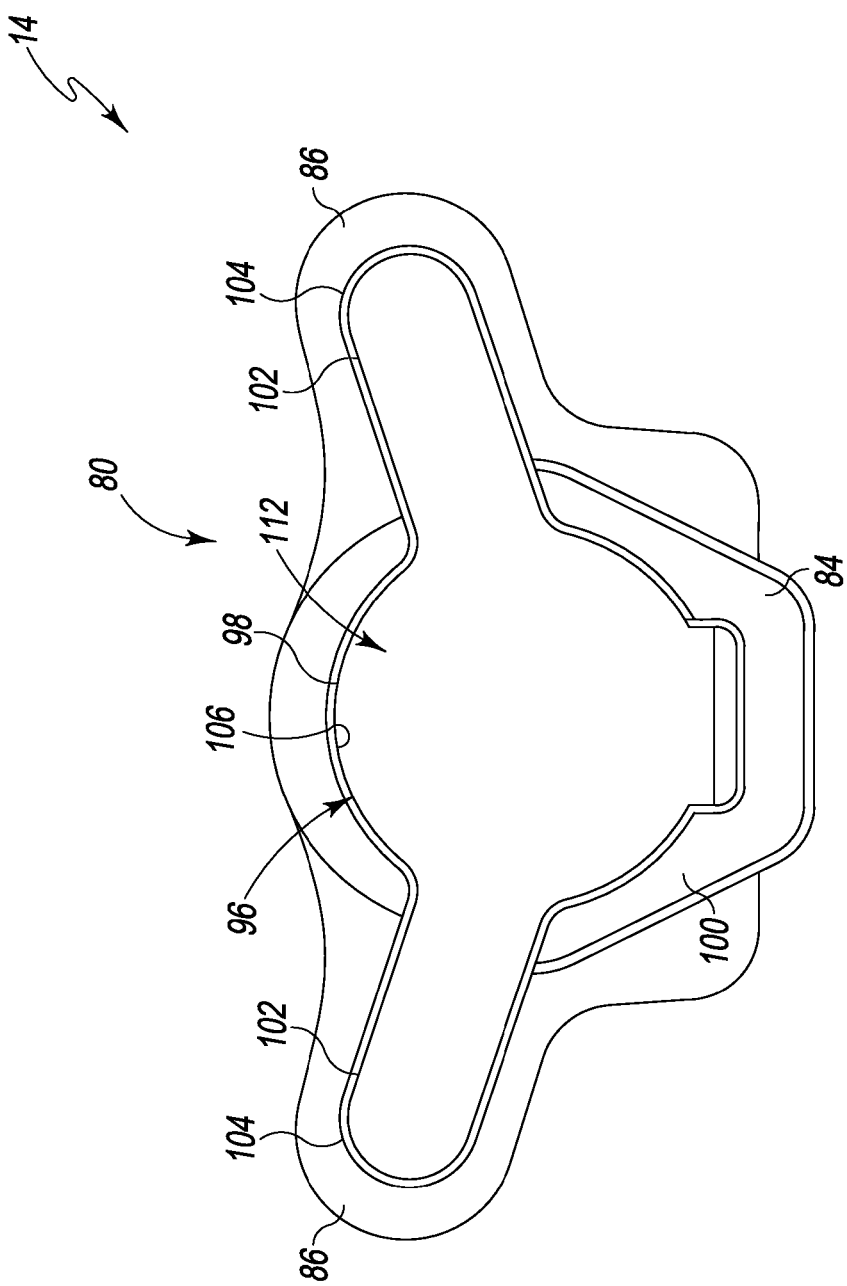
FIG. 5 a top plan view of the guide tower of FIG. 4.

As shown in FIG. 5, the tower base 80 has an upper guide opening 96 defined therein. The upper guide opening 96 includes a central opening 98 defined in an upper surface 100 of the main body 84 and a pair of elongated openings 102 defined in the respective inclined upper surfaces 104 of the arms 86. The tower base 80 has an inner wall 106 that extends downwardly from the upper guide opening 96 to a lower guide opening 110 (see FIG. 4) defined in the bottom surface 88. The inner wall 106 defines a vertically-extending passageway 112 through the main body 84 and the arms 86. The cross-sectional shape of the passageway 112 of the tower base 80 substantially matches the cross-sectional shape of the passageway 46 of the base trial 12. When the guide tower 14 is properly positioned on the base trial 12, the passageways 46, 112 are substantially aligned. In that way, the configuration of the passageway 112, like the configuration of the passageway 46, permits the advancement of various surgical drills, punches, and other instruments into the proximal end 20 of the patient's resected tibia 22, as will be described in greater detail below.

Returning now to FIG. 4, the main body 84 of the tower base 80 has an anterior surface 114 extending upwardly from the bottom surface 88 of the tower base 80. The anterior surface 114 has a pair of openings 116, 118 defined therein. The opening 116 is trapezoidal-shaped and extends upwardly from the bottom surface 88. A number of sidewalls 120 extend inwardly from the lower opening 116 to define an aperture 122. As best seen in FIG. 1, the aperture 122 extends between the anterior surface 114 of the main body 84 and an interior surface 124 of the main body 84 such that the aperture 122 is in communication with the passageway 112. The aperture 122 is also connected to the lower guide opening 110.

The opening 118 of the tower base 80 is rectangular-shaped and is positioned above the lower opening 116. A number of sidewalls 126 extend inwardly from the opening 118 to define another aperture 128 in the main body 84. Like the aperture 122, the aperture 128 extends between the anterior surface 114 and the interior surface 124 such that the aperture 128 is in communication with the passageway 112. It should be appreciated that in other embodiments the openings 116, 118 may be modified to, for example, have different shapes. Additionally, it should be appreciated that in other embodiments the guide tower 14 may include only one opening or may include additional openings in the main body 84 and/or the arms 86.

The guide tower 14 also includes a flange 130 projecting outwardly from the anterior surface 114 and the pair of fixation pins 82 that extend downwardly from the anterior aspect 90 of the bottom surface 88. The flange 130 is positioned above the opening 118 and below the upper surface 100 of the main body 84. The fixation pins 82 extending from the bottom surface 88 are sized to be received in a corresponding pair of fixation pin holes 92 of the fastener holes 72 defined in the base trial 12. Each fixation pin 82 includes an upper section 132 and a lower section 134 extending downwardly from the upper section 132. The upper section 132 has a diameter 136 and the lower section 134 has a diameter 138. In the illustrative embodiment, the diameter 138 is less than the diameter 136 such that the lower section 134 is narrower than the upper section 132 of the fixation pin 82. Each fixation pin 82 further includes a pointed conical tip 140 configured to engage the proximal end 20 of the patient's tibia 22. It should be appreciated that in other embodiments the guide tower 14 may include additional or fewer fixation pins 82.

Returning to FIG. 1, the assembly 10 also includes the drill stop 18 that is configured to be positioned on tower base 80. The drill stop 18 includes a hexagonal-shaped body 150 and a pair of tabs 152 extending downwardly from a lower end 154 of the body 150. The drill stop 18 has an outer rim 156 that extends outwardly from the upper end 158 of the body 150. A circular opening 160 defined in the body 150 has an inner wall 162 extending downwardly therefrom. A passageway 164, which extends through the body 150, is defined by the inner wall 162. When the drill stop 18 is properly positioned on the guide tower 14, the passageway 164 is substantially aligned with the central opening 98 of the guide tower 14. Additionally, the drill stop 18 and the guide tower 14 together define a height 166 (see FIG. 16), which may correspond to a drilled-hole depth in the patient's tibia 22, as described in greater detail below.

The downward-extending tabs 152 of the drill stop 18 are configured to be positioned in the upper guide opening 96 of guide tower 14 when the drill stop 18 is properly positioned on the tower base 80. In the illustrative embodiment, the tabs 152 are sized to be positioned between the anterior section 144 and posterior section 146 of the inner wall 106 of the tower base 80 when the lower end 154 of the body 150 of the drill stop 18 is positioned on the upper surface 100 of the guide tower 14 (see FIG. 16). It should be appreciated that in other embodiments the tabs 152 may be omitted or take different forms. Similarly, it should also be appreciated that in other embodiments the body 150 may have a rectangular or cylindrical shape.

In the illustrative embodiment, the base trial 12 and the guide tower 14 are formed from an implant-grade metallic material such as steel, titanium, or cobalt chromium. The drill stop 18 is formed from a stiff elastomeric material such as, for example, vulcanized rubber. It will be appreciated that in other embodiments the drill stop 18 may be formed from a polymeric material such as polyethylene or ultra-high molecular weight polypropylene (UHMWP).

Figure 6:
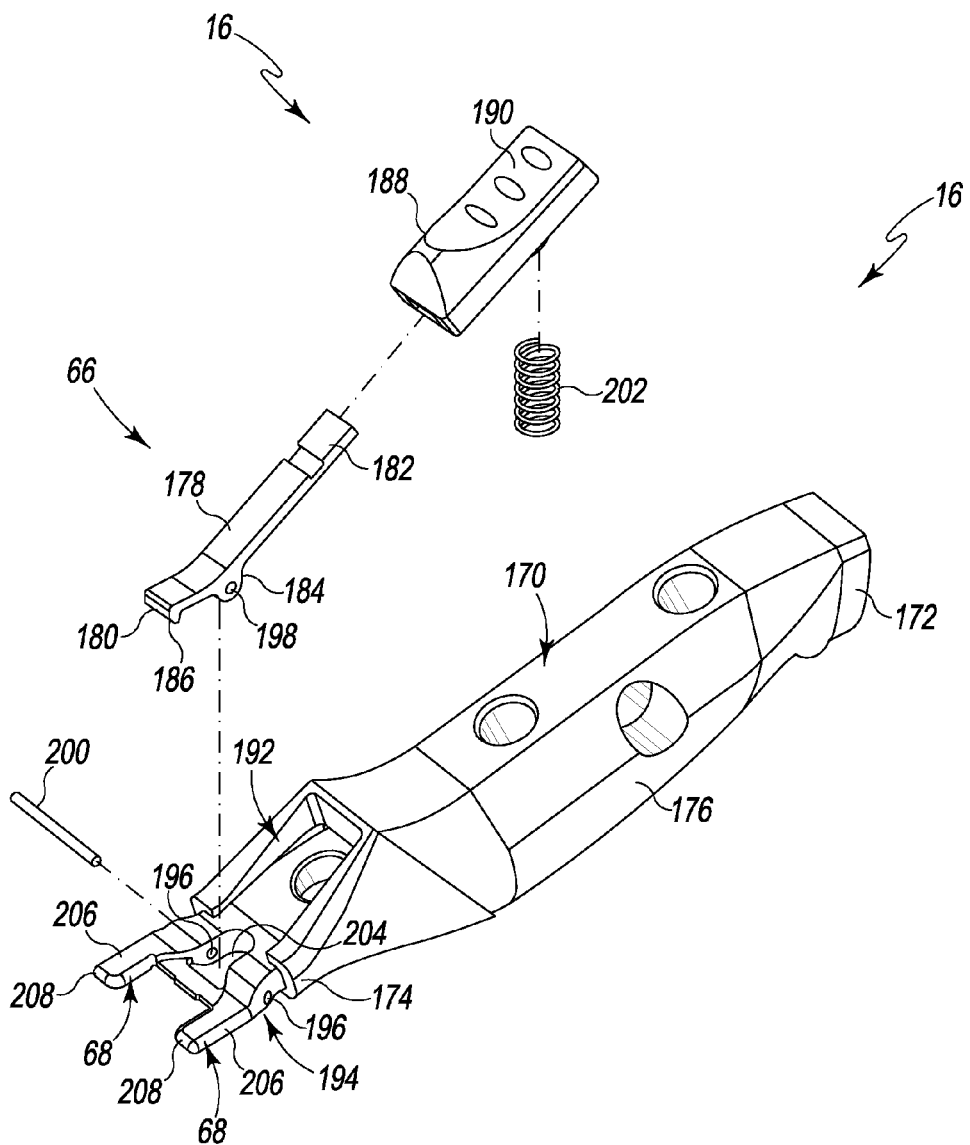
FIG. 6 is an exploded, perspective view of the alignment handle of the orthopaedic surgical assembly of FIG. 1.
Figure 7:
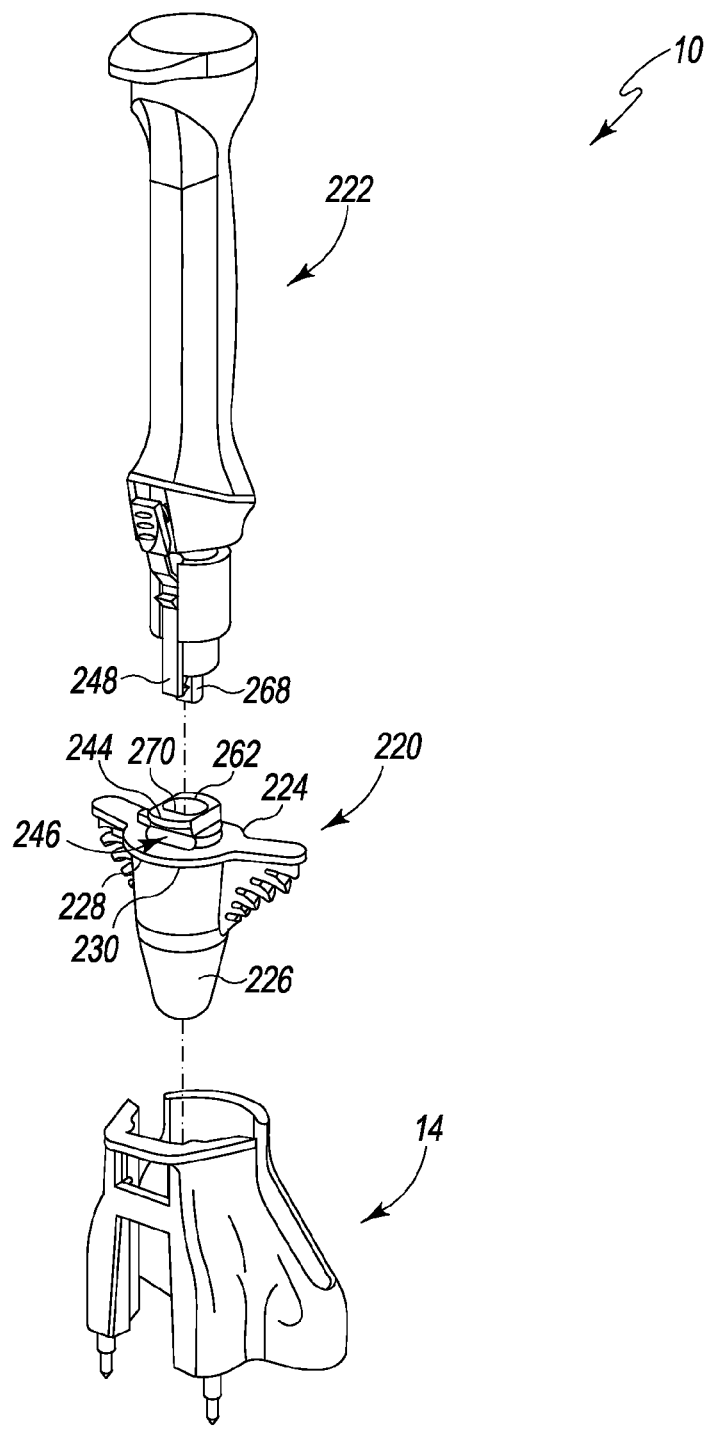
FIG. 7 is an exploded, perspective view of showing the guide tower, a keel punch, and an impaction handle of the orthopaedic surgical instrument assembly of FIG. 1.

As described above, the assembly 10 further includes the detachable alignment handle 16, which the surgeon may use to adjust the position of the base trial 12. Referring now to FIG. 6, the alignment handle 16 includes an elongated body 170 and the lever 66, which is pivotally coupled to elongated body 170. The elongated body 170 has a back end 172 and a front end 174, and a grip 176 is positioned therebetween.

The lever 66 of the alignment handle 16 includes a rocker arm 178 having a latching end 180, an actuation end 182, and a mounting bracket 184 positioned between the ends 180, 182. A flange or catch 186 extends downwardly from the rocker arm 178 at the latching end 180. The catch 186 is sized to be received in the slot 60 of the base trial 12. The lever 66 also includes a user-operated button 188 that is secured to the rocker arm 178 at the actuation end 182. In the illustrative embodiment, the button 188 includes a contoured outer surface 190 that is configured to receive a fingertip of a surgeon or other user.

The front end 174 of the elongated body 170 has a channel 192 defined therein that is sized to receive the lever 66. The lever 66 is pivotally coupled to the body 170 via a joint 194, which includes a pair of openings 196 defined in the elongated body 170 and a through-hole 198 defined in the mounting bracket 184 of the lever 66. A cylindrical pin 200 is positioned in the openings 196 and the through-hole 198 to join the lever 66 with the body 170. A biasing element, illustratively embodied as a spring 202, is positioned between actuation end 182 of the rocker arm 178 and the bottom surface 204 of the channel 192.

As shown in FIG. 6, the pins 68 are positioned on each side of the lever 66. Each pin 68 has a body 206 that extends outwardly from the front end 174 of the elongated body 170 to a tip 208. The body 206 has an oblong-shaped cross section that corresponds to the oblong-shape of the apertures 64 defined in the base trial 12. As described above, each pin 68 is configured to be received in a corresponding to aperture 64 defined in the base trial 12.

In use, the alignment handle 16 may be secured to the base trial 12 by positioning the tips 208 of the pins 68 in the apertures 64 defined in the base trial 12. The pins 68 may be then advanced into the apertures 64 to bring the inclined front surface of the catch 186 into contact with the sidewall 36 of the base trial 12. The bias exerted by the spring 202 may be overcome by pressing down on the button 188, thereby causing the lever 66 to pivot about joint 194 and aligning the catch 186 with the channel 58 of the notch 54 defined in the base trial 12. The latching end 180 of the lever 66 may then be advanced into the notch 54. When the latching end 180 of the lever 66 is positioned at the posterior end 62 of the notch 54, the catch 186 is positioned over the oblong-shaped slot 60. After the button 188 is released, the spring 202 urges the lever 66 to pivot such that the catch 186 is advanced into the slot 60, thereby securing the base trial 12 to the alignment handle 16.

As shown in FIGS. 7-10, the orthopaedic surgical instrument assembly 10 further includes a keel punch 220 and a detachable impaction handle 222. The keel punch 220 is configured to be inserted through the plate opening 38 of the base trial 12 into the proximal end 20 of the patient's tibia 22 to prepare the patient's tibia for implantation of a tibial tray or other prosthetic component. The keel punch 220 has an upper frame 224 and a main body 226 extending downwardly therefrom. The upper frame 224 and the main body 226 cooperate to define a rim 228 around the periphery thereof. The rim 228 has a bottom surface 230 configured to engage the shelf surface 52 of the base trial 12 when the keel punch 220 is seated on the base trial 12 and in the proximal end 20 of the patient's tibia 22.

Figure 8:
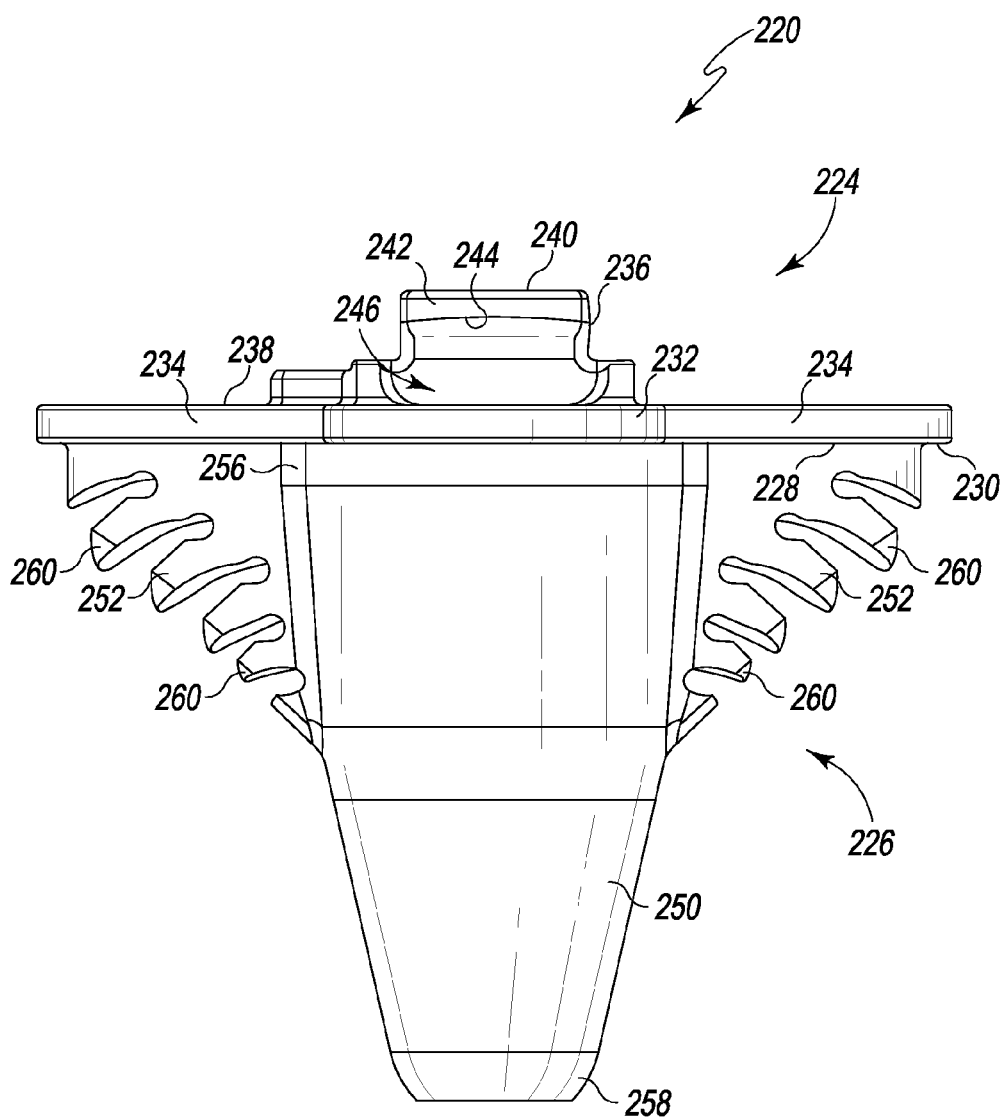
FIG. 8 is an anterior side elevation view of the keel punch shown in FIG. 7.

As shown in FIG. 8, the upper frame 224 of the keel punch 220 includes a central platform 232 and a pair of arms 234 extending outwardly from the central platform 232. A post 236 extends upwardly from the upper surface 238 of the upper frame 224 to a top end 240, and a lip 242 extends outwardly from the top end 240. The lip 242 has a bottom surface 244 that extends substantially parallel to the upper surface 238. The bottom surface 244 and the upper surface 238 of the central platform 232 cooperate to define a lever-receiving notch 246. The lever-receiving notch 246 is configured to receive a locking flange 248 associated with the impaction handle 222, as described in greater detail below.

The main body 226 of the keel punch 220 includes a central bullet 250 and a pair of lower arms 252 that are positioned below the arms 234 and extend outwardly from the central bullet 250. The central bullet 250 has circular cross-section that varies in diameter along its length (i.e., the diameter of the bullet 250 tapers in the superior-inferior direction). In that way, the cross-sectional diameter of the bullet 250 at its upper end 256 is greater than the cross-sectional diameter of the bullet 250 at its lower end 258. A number of downwardly extending teeth 260 are defined in each of the lower arms 252. The teeth 260 are configured to engage the patient's tibia 22 to define an opening 404 in the proximal end 20 of the patient's tibia 22 sized to receive the tibial implant (see FIG. 26).

Figure 9:
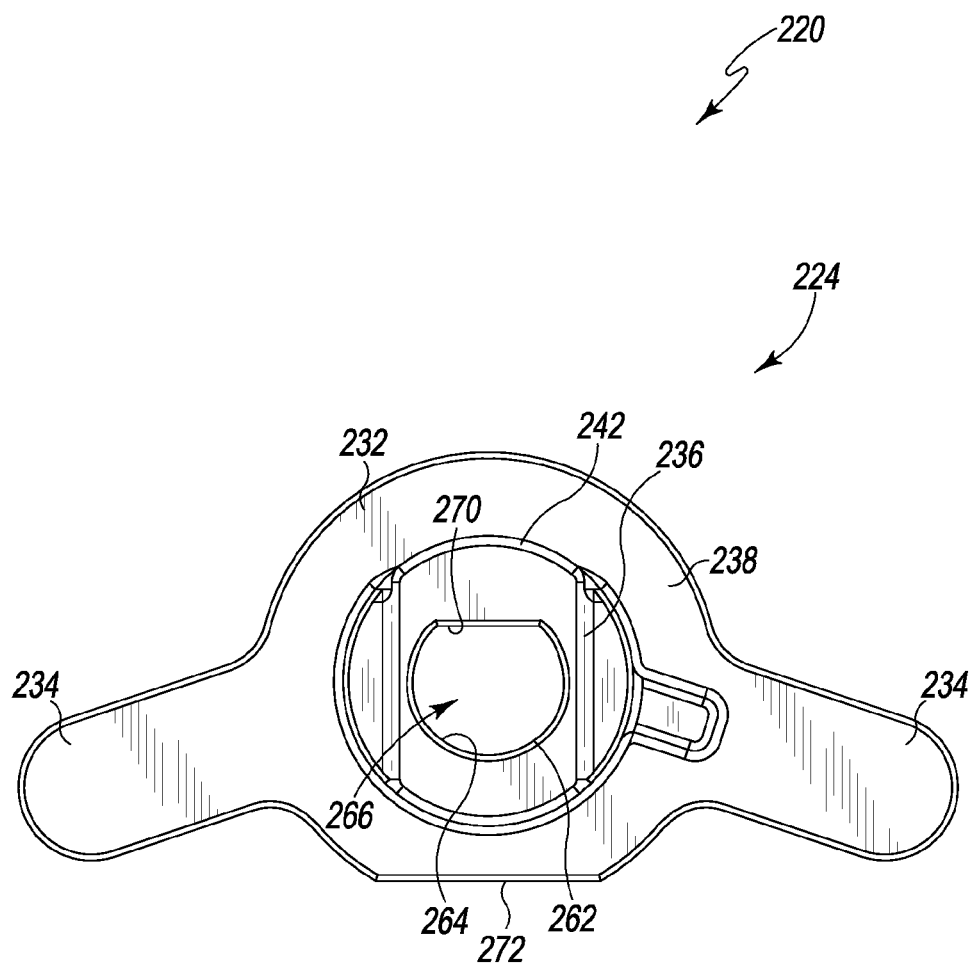
FIG. 9 is a top plan view of the keel punch of FIG. 8.

As shown in FIG. 9, the post 236 of the keel punch 220 has an opening 262 defined therein. An inner wall 264 extends downwardly from the opening 262 to define a central passageway 266 through the keel punch 220. The opening 262 is configured to receive a guide pin 268 associated with the impaction handle 222 (see FIG. 7). The inner wall 264 has a keyed section 270 that permits the keel punch 220 to be attached to the impaction handle 222 at only a single predetermined orientation.

The central platform 232 of upper frame 224 also has keyed section 272. The keyed section 272 and the orientation of the arms 234 relative to the platform 232 permit the keel punch 220 to be inserted into the plate opening 38 of the base trial 12 in a predetermined orientation.

Figure 10:
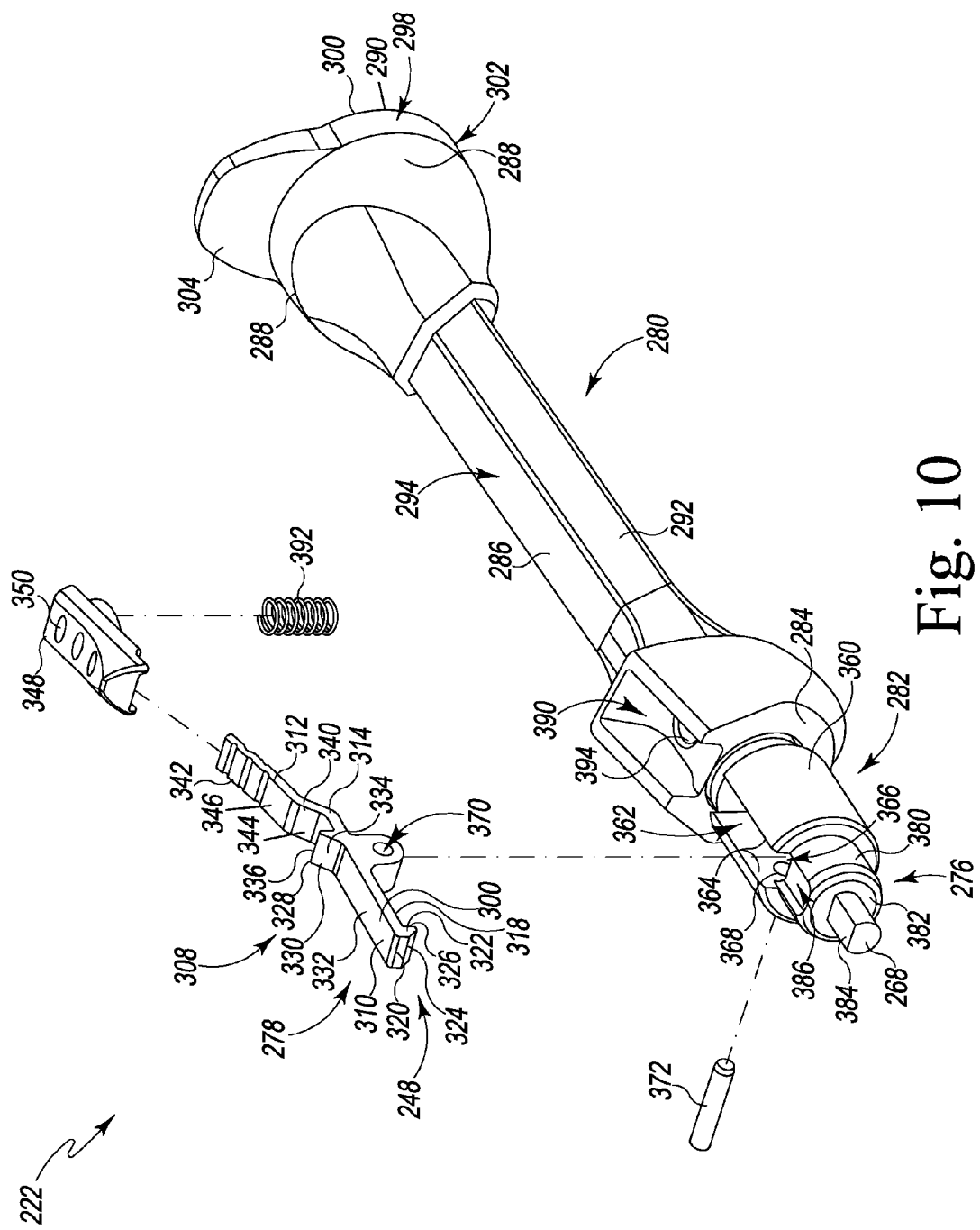
FIG. 10 is an exploded, perspective view of the impaction handle shown in FIG. 7.

As described above, the assembly 10 also includes the impaction handle 222, which may be removably attached to the keel punch 220 and/or the guide tower 14. Referring now to FIG. 10, the impaction handle 222 includes an elongated body 280, a mounting shaft 282 connected to an end 284 of the elongated body 280, and an attachment mechanism 278 configured to attach the keel punch 220 and/or the guide tower 14 to the attachment end 276 of the handle 222. The elongated body 280 includes a neck 286 extending from the end 284 and a head 288 connected to the neck 286 at the opposite end 290 of the elongated body 280. A grip 292 is secured to the neck 286 between the ends 284, 290 and is configured to receive the hand of a surgeon or other user. The grip 292 has a cross-sectional area 294.

The head 288 of the impaction handle 222 includes a metal plate 298 positioned at the end 290. The metal plate 298 includes a circular base 300 that has a cross-sectional area 302 that is greater than the cross-sectional area 294 of the grip 292. In use, the surgeon holds the impaction handle 222 via the grip 292 and strikes the metal plate 298 with a mallet, sledge, or other impaction tool to drive the keel punch 220 into the proximal end 20 of the patient's tibia 22. Because the circular base 300 has a cross-sectional area 302 that is greater than the cross-sectional area 294 of the grip 292, the circular base 300 shields the hand of the surgeon using the grip 292. The metal plate 298 also includes a flange 304 extending outwardly from the circular base 300, which cooperates with the base 300 to shield the hand of the surgeon.

The attachment mechanism 278 of the impaction handle 222 includes a lever 308 pivotally coupled to the mounting shaft 282. The lever 308 includes a latching arm 310 and an actuation arm 312 extending at an angle from an end 314 of the latching arm 310. A mounting bracket 316 is secured to the bottom surface 318 of the latching arm 310 between the end 314 and the opposite end 320.

The locking flange 248 is positioned at the end 320 of the latching arm 310 and extends downwardly from the bottom surface 318 of the latching arm 310. As described above, the locking flange 248 is configured to engage the lip 242 of the keel punch 220 to secure the keel punch 220 to the impaction handle 222. The locking flange 248 has a wedge-shaped body 322 that includes an inclined front face 324 and a rear face 326 extending orthogonal to the bottom surface 318 of the latching arm 310. When the keel punch 220 is secured to the impaction handle 222, the rear face 326 contacts the bottom surface 244 of the lip 242 (see FIG. 17).

Another locking flange or catch 328 is positioned adjacent to the end 314 of the latching arm 310 such that the mounting bracket 316 is positioned between the flange 248 and the catch 328. As will be described in greater detail below, the opening 118 of the guide tower 14 is sized to receive the catch 328 such that the guide tower 14 may be secured to the impaction handle 222. As shown in FIG. 10, the catch 328 includes a wedge-shaped body 330 that extends upwardly from the top surface 332 of the latching arm 310 in a direction opposite the locking flange 248. The body 330 has an inclined front face 334 and a rear face 336 that extends orthogonal to the top surface 332 of the latching arm 310. When the guide tower 14 is secured to the impaction handle 222, the rear face 336 contacts the upper sidewall 338 of the guide tower 14 (see FIG. 25).

The actuation arm 312 of the lever 308 is divided into two branches 340, 342 that are angled relative to the latching arm 310. The branch 340 extends away from the end 314 of the latching arm 310, while the branch 342 extends from the branch 340. The branches 340, 342 have inclined top surfaces 344, 346, respectively, that are angled relative to the top surface 332 of the latching arm 310 and one another. The lever 308 also includes a user-operated button 348 that is secured to the branch 342. In the illustrative embodiment, the button 348 includes a contoured outer surface 350 that is configured to receive a fingertip of a surgeon or other user.

The mounting shaft 282 of the impaction handle 222 includes a housing 360 extending from the end 284 of the elongated body 280. The housing 360 has a channel 362 defined by a pair of sidewalls 364. The channel 362 is sized to receive the lever 308, and the lever 308 is pivotally coupled to the housing 360 via a joint 366. The joint 366 includes a pair of openings 368 defined in the sidewalls 364 and a throughhole 370 defined in the mounting bracket 316. A cylindrical pin 372 is positioned in the openings 368 and the throughhole 370 such that the lever 308 is joined with the housing 360. As shown in FIG. 10, the joint 366 is positioned between the locking flange 248 and the catch 328 of the lever 308.

The mounting shaft 282 also includes a rod 380, which extends from the housing 360. The guide pin 268 extends from an end face 382 of the rod 380. The cross-sectional areas of the housing 360, rod 380, and guide pin 268 are progressively smaller. In that way, the attachment end 276 of the impaction handle 222 is stepped. The guide pin 268 has a cross-section that substantially matches the shape of the opening 262 defined in the keel punch 220. As shown in FIG. 10, the guide pin 268 includes a flat face 384 that is sized to be received in the keyed section 270 of the keel punch 220.

The rod 380 of the mounting shaft 282 has a channel 386 defined therein substantially aligned with the channel 362 defined in the housing 360. The latching arm 310 of the lever 308 is positioned in, and extends outwardly from, the channels 362, 386, and the end 320 of the latching arm 310 is positioned beyond the end face 382 of the rod 380 such that the locking flange 248 is positioned over the guide pin 268 and extends toward the flat face 384. This arrangement permits the locking flange 248 to be positioned in notch 246 of the keel punch 220 and the guide pin 268 to be positioned in the opening 262 of the keel punch 220 to secure the keel punch 220 to the impaction handle 222.

As shown in FIG. 10, the neck 286 of the elongated body 280 has a channel 390 defined therein that is sized to receive the actuation arm 312 of the lever 308. The impaction handle 222 also includes a biasing element, illustratively embodied as a spring 392, which is positioned between actuation arm 312 and the bottom surface 394 of the channel 390.

To secure the keel punch 220 to the impaction handle 222, the guide pin 268 is positioned in the opening 262 of the keel punch 220. By pressing down on the user-operated button 348 of the lever 308 with a predetermined amount of force, the bias exerted by the spring 392 may be overcome, thereby causing the lever 308 to pivot about the joint 366. As the lever 308 is pivoted, the bottom surface 318 of the lever 308 is moved out of the channel 386 of the rod 380 and the locking flange 248 is moved away from the flat face 384 of the guide pin 268.

The guide pin 268 may be advanced along the passageway 266 defined in the keel punch 220 until the post 236 of the keel punch 220 is placed in contact with the end face 382 of the rod 380. In that position, the locking flange 248 is positioned over the lever-receiving notch 246. When the button 348 is released, the spring 392 urges the lever 308 to pivot about the joint 366 and the locking flange 248 is advanced into the notch 246 of the keel punch 220. In particular, the lip 242 of the keel punch 220 is positioned between the locking flange 248 and the end face 382 of the rod 380, while the guide pin 268 of the impaction handle 222 is positioned in the opening 262 of the keel punch 220. The keel punch 220 is thereby secured to the impaction handle 222.

It will be appreciated that one or more of the instruments described above in regard to assembly 10 may be omitted or modified. For example, in some embodiments, the upper surface 100 of the guide tower 14 may function as a drill stop such that the drill stop 18 is unnecessary. Additionally, for example, the base trial 12 may be manufactured without the alignment etchings 70 or with fewer fastener holes 72.

Figure 11:
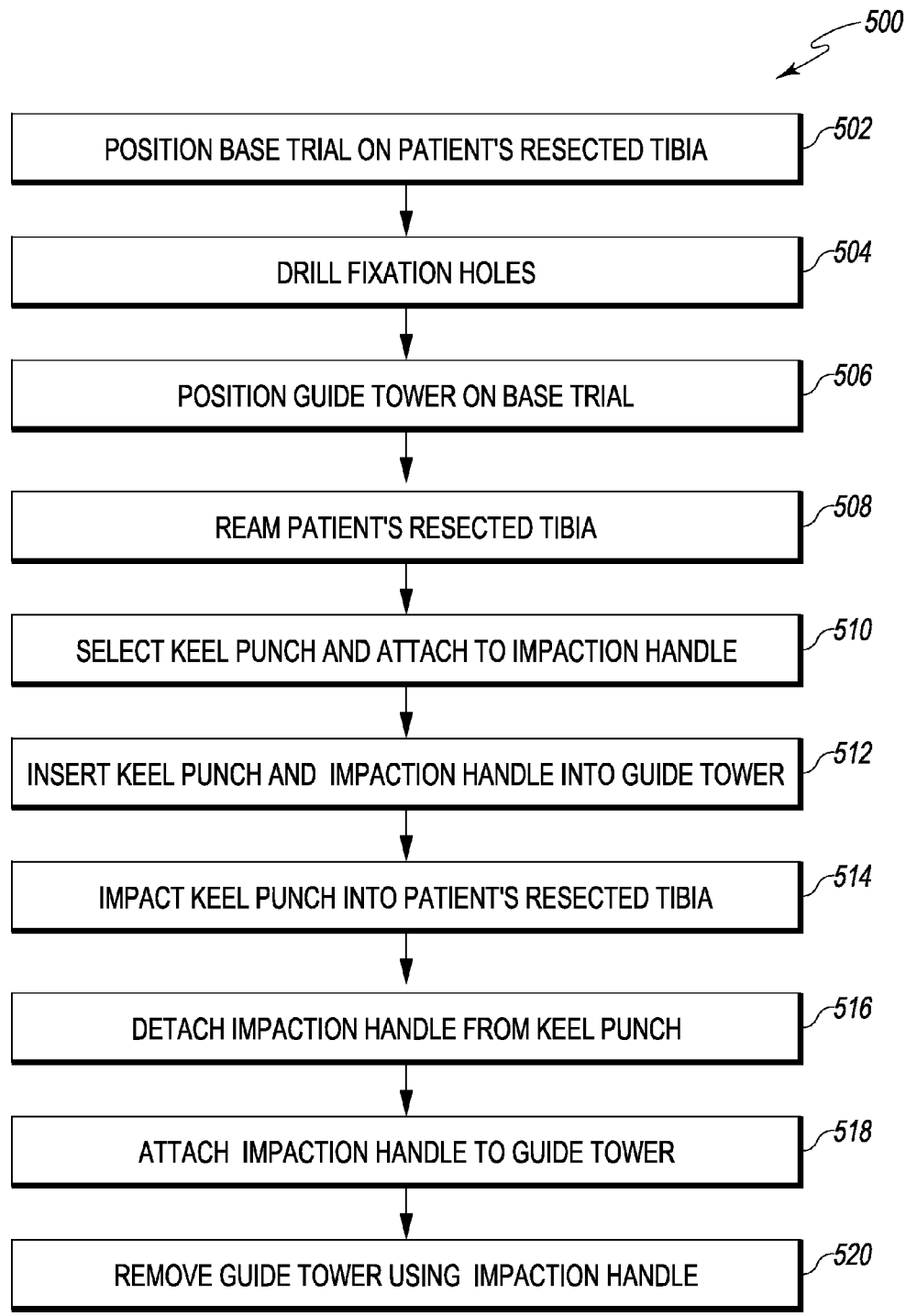
FIG. 11 is a simplified flow chart of one embodiment of a procedure for using the orthopaedic surgical instrument assembly of FIGS. 1-10.

In operation, the orthopaedic surgical instrument assembly 10 is utilized during the performance of an orthopaedic surgical procedure like that shown in FIG. 11. As shown in FIGS. 12-25, the tibial base trial 12 and the guide tower 14 are positioned on the resected surface 400 of the proximal end 20 of the patient's tibia 22, and the surgeon uses the trial 12 and the tower 14 to guide, for example, a surgical drill while reaming the proximal end 20 of the patient's tibia 22. Thereafter, the keel punch 220 is impacted into the proximal end 20 of the patient's tibia 22 before the guide tower 14 is removed.

Figure 12:
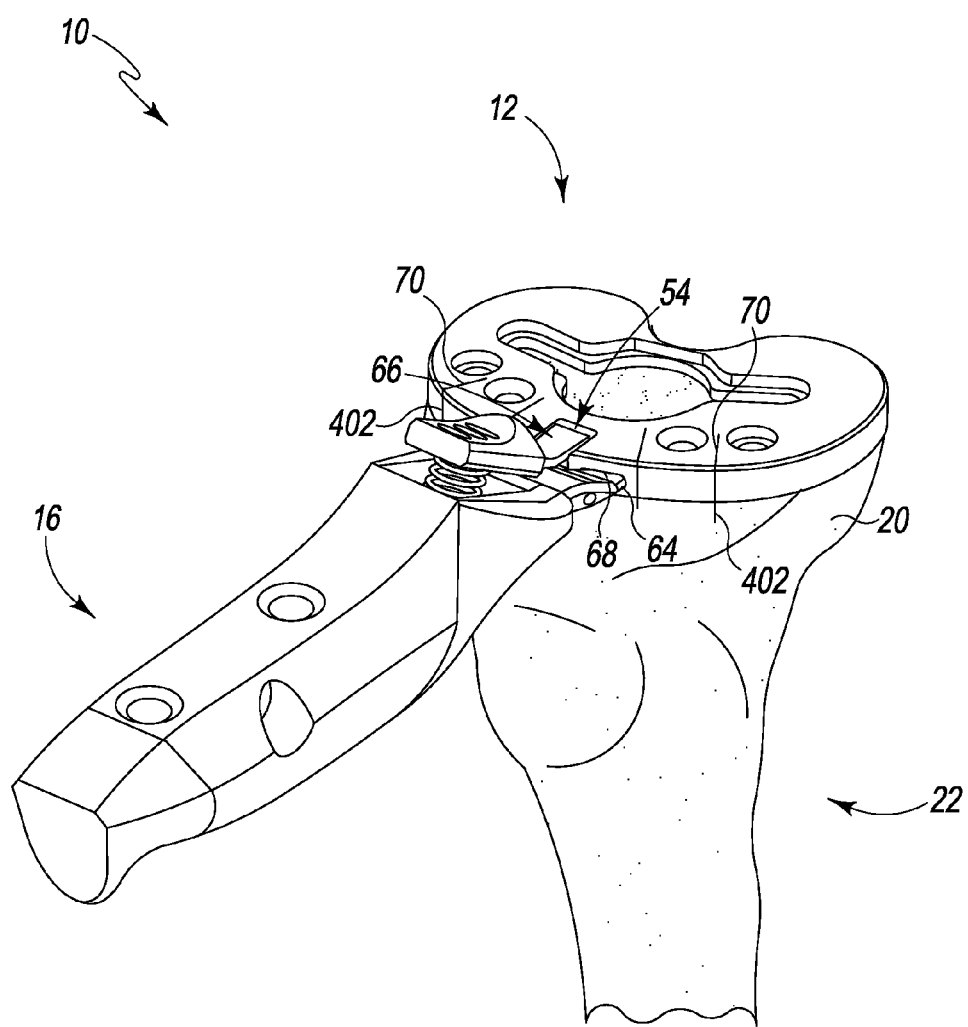
FIGS. 12-25 are views of a patient's tibia and the orthopaedic surgical instrument assembly of FIGS. 1-10 as the orthopaedic surgical instrument assembly is used in the procedure of FIG. 11.

Referring now to FIG. 11, an illustrative orthopaedic surgical procedure 500 using the surgical instrument assembly 10 is shown. In block 502, the surgeon positions the tibial base trial 12 on the resected surface 400 of the proximal end 20 of the patient's tibia 22. To do so, the surgeon may attach the alignment handle 16 to the base trial 12 and, as shown in FIG. 12, use the alignment handle 16 to position the base trial 12 on the resected surface 400 and align the alignment etchings 70 with one or more marks 402 made on the proximal end 20 of the patient's tibia 22. Alternatively, the surgeon may choose to position the base trial 12 by hand.

When using the alignment handle 16, the surgeon first attaches the alignment handle 16 to the base trial 12. To do so, the surgeon positions the tips 208 of the pins 68 extending from the alignment handle 16 in the apertures 64 defined in the base trial 12. The surgeon may press on the button 188 to overcome the bias exerted by the spring 202, thereby causing the lever 66 to pivot about joint 194 and aligning the catch 186 with the channel 58 of the notch 54 defined in the base trial 12. The surgeon advances the latching end 180 of the lever 66 into the notch 54. When the latching end 180 of the lever 66 is positioned at the posterior end 62 of the notch 54, the catch 186 is positioned over the oblong-shaped slot 60. When the surgeon releases the button 188, the spring 202 urges the lever 66 to pivot such that the catch 186 is advanced into the slot 60, thereby securing the base trial 12 to the alignment handle 16.

After aligning the alignment etchings 70 of the base trial 12 with one or more marks 402 made on the proximal end 20 of the patient's tibia 22, the procedure advances to block 504 in which the surgeon uses the fastener holes 72 defined in the base trial 12 to drill a number of openings in the proximal end 20 of the patient's tibia 22. After drilling the desired number of holes, the procedure advances to block 506.

Figure 13:
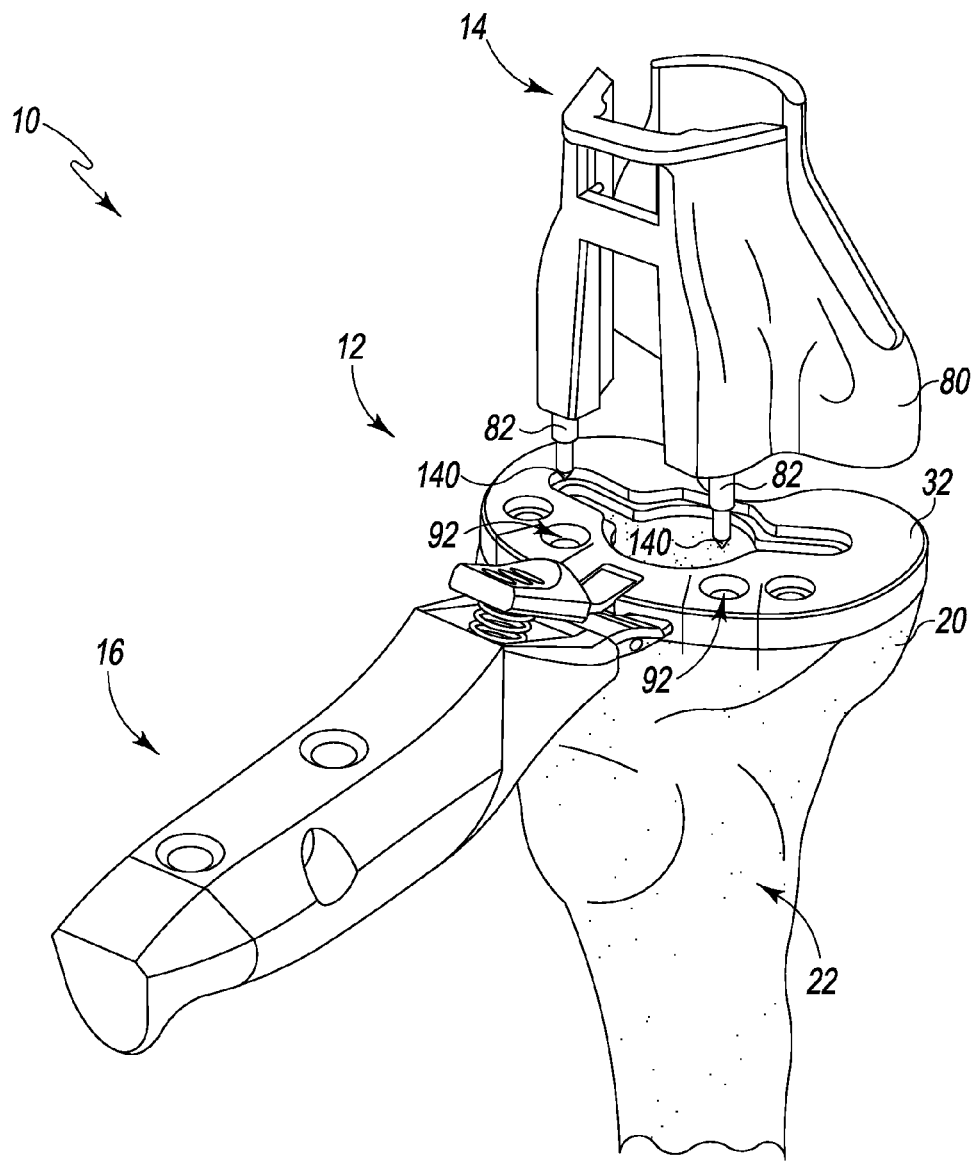

In block 506, the guide tower 14 is placed on the base trial 12. To do so, the surgeon positions the tower base 80 over the base trial 12. As shown in FIG. 13, the surgeon aligns the fixation pins 82 extending from the tower base 80 with the fixation pin holes 92 defined in the base trial 12. The surgeon advances the fixation pins 82 into the pin holes 92 of the base trial 12 such that the conical tips 140 of the pins 82 are positioned in the openings drilled in the proximal end 20 of the patient's tibia 22. The surgeon continues to advance the fixation pins 82 into the openings while lowering the tower base 80 into contact with the upper surface 32 of the base trial 12.

Figure 14:
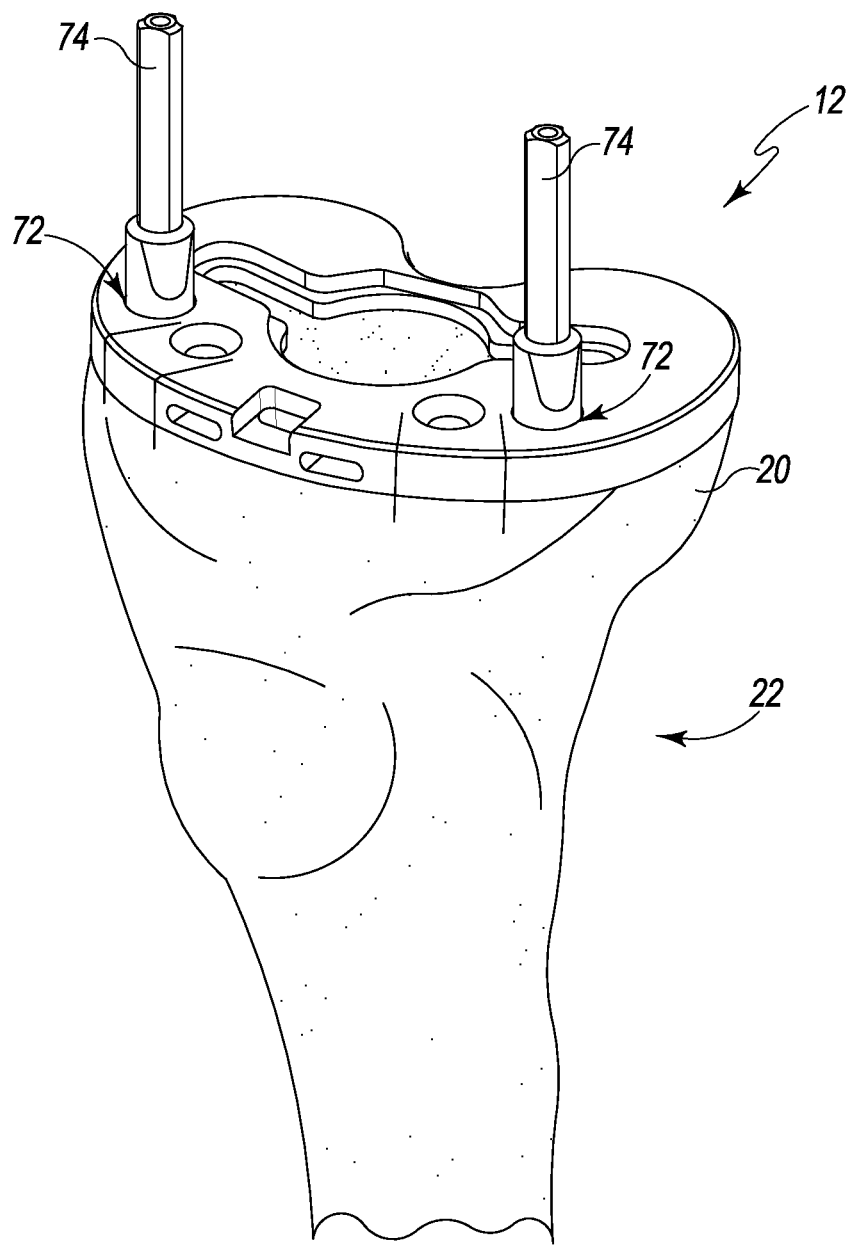

As shown in FIG. 14, the surgeon may optionally insert one or more additional fixation pins 74 into the proximal end 20 of the patient's tibia 22. To do so, the surgeon drills an additional number of openings in the resected proximal end 20 of the patient's tibia 22. The surgeon then advances the fixation pins 74 through the fastener holes 72 and into the proximal end 20 of the patient's tibia 22 to secure the tibial base trial 12 to the patient's tibia 22. It should be appreciated that the surgeon can attach the additional fixation pins before or after positioning the guide tower 14 on the base trial 12.

Returning now to FIG. 11, the procedure 500 continues with block 508 in which surgeon reams the patient's tibia 22. To do so, the surgeon may use, for example, the surgical drill 410 shown in FIG. 15. The surgical drill 410 is advanced through the upper guide opening 96 defined in the guide tower 14 and along passageway 112. The drill 410 then passes through the central opening 40 of the base trial 12 and into engagement with the patient's tibia 22. The surgeon then operates the drill 410 to create a drilled-hole 412 in the proximal end 20 of the patient's tibia 22 using the guide tower 14 and the base trial 12 as a guide assembly to maintain the drill 410 in the proper orientation relative to the patient's tibia 22.

Figure 15:
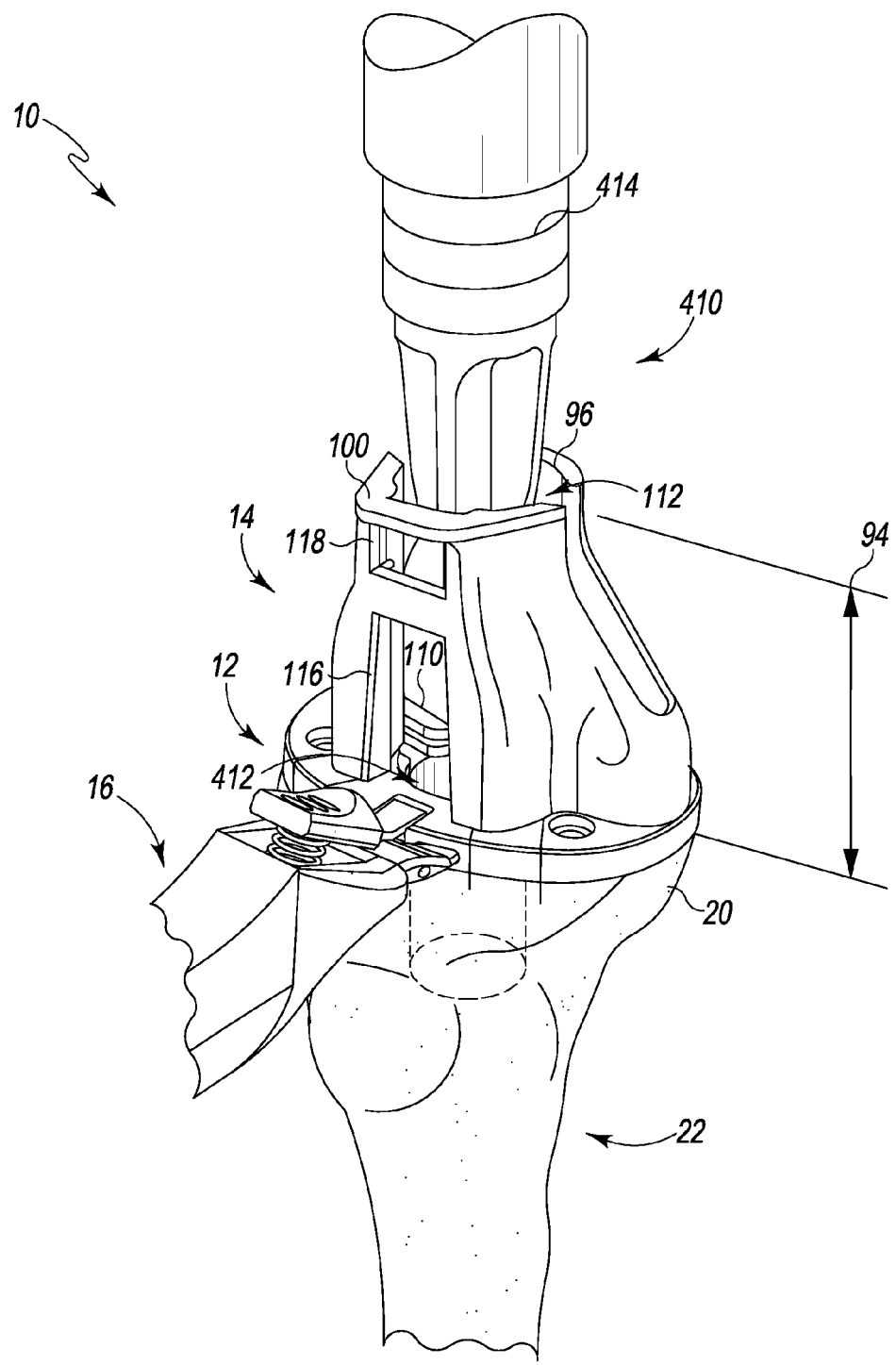

As shown in FIG. 15, the drill 410 includes a plurality of horizontal lines 414, each of which corresponds to a different depth for the drilled-hole 412. The surgeon may advance the drill 410 into the proximal end 20 of the patient's tibia 22 until the one of the horizontal lines 414 corresponding to the desired depth is aligned with the upper surface 100 of the guide tower 14. In that way, the horizontal lines 414 and the height 94 of the guide tower 14 cooperate to limit the drill 410 to a predetermined drill hole depth. It should be appreciated that in other embodiments the drill 410 may also include a depth stop that engages the upper surface 100 when the drill 410 has advanced to the desired depth in the patient's tibia 22.

Figure 16:
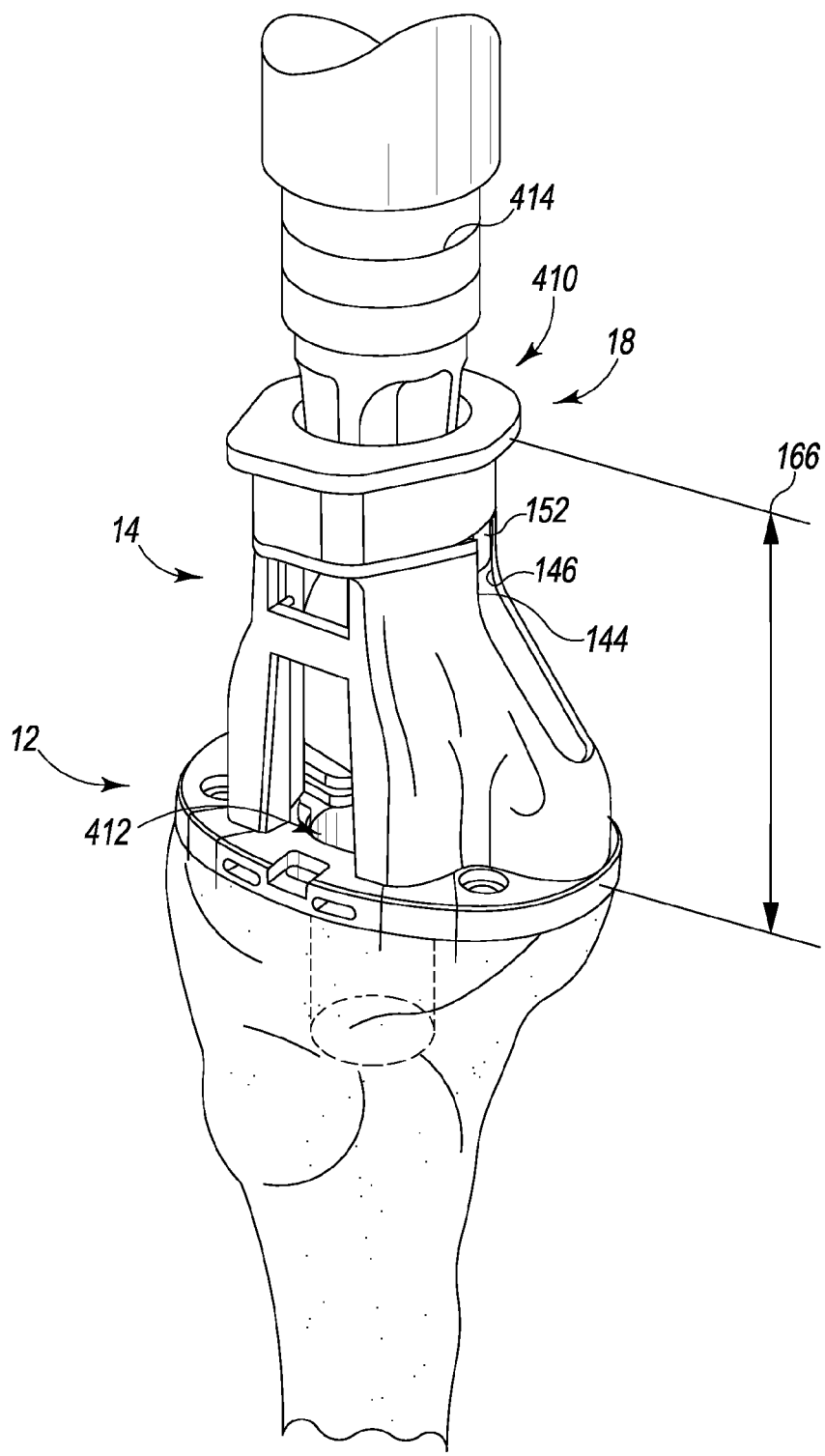

As shown in FIG. 16, the surgeon may optionally use the drill stop 18 to guide the reaming process. To do so, the drill stop 18 is positioned on the guide tower 14. The surgeon may advance the drill 410 into the patient's tibia 22 until one of the horizontal lines 414 corresponding to the desired depth is aligned with the upper surface of the drill stop 18. In that way, the horizontal lines 414 and the combined height 166 of the guide tower 14 and the drill stop 18 cooperate to limit the drill 410 to another predetermined drilled-hole depth. It should be appreciated that in other embodiments the drill 410 may also include a depth stop that may be used separately from, or in combination with, the drill stop 18 to permit the drill 410 to advance to the desired depth in the patient's tibia 22.

Because debris generated by the reaming process may prevent the keel punch 220 from properly seating on the base trial 12, the surgeon may flush the guide tower 14 and the drilled-hole 412 after reaming. To do so, the surgeon may spray fluid into the upper guide opening 96, through the passageway 112, and into the drilled-hole 412. Additionally, the surgeon may utilize the openings 116, 118 defined in the guide tower 14 to apply fluid to the interior of the assembly 10 and into the drilled-hole 412. Because the opening 116 of the tower 14 is in communication with the lower guide opening 110, the opening 116 also provides a path for the debris to flow out of the assembly 10 and the drilled-hole 412, thereby providing additional support for the flushing process.

Returning now to FIG. 11, the surgeon selects a keel punch 220 in block 510 of the procedure 500. The surgeon may select an appropriately-sized keel punch 220 from a plurality of keel punches included in, for example, a surgical kit. Alternatively, the size of the keel punch 220 may be predetermined and the surgical kit may include only one keel punch. In that case, the surgeon merely selects the only keel punch 220 included in the surgical kit.

Figure 17:
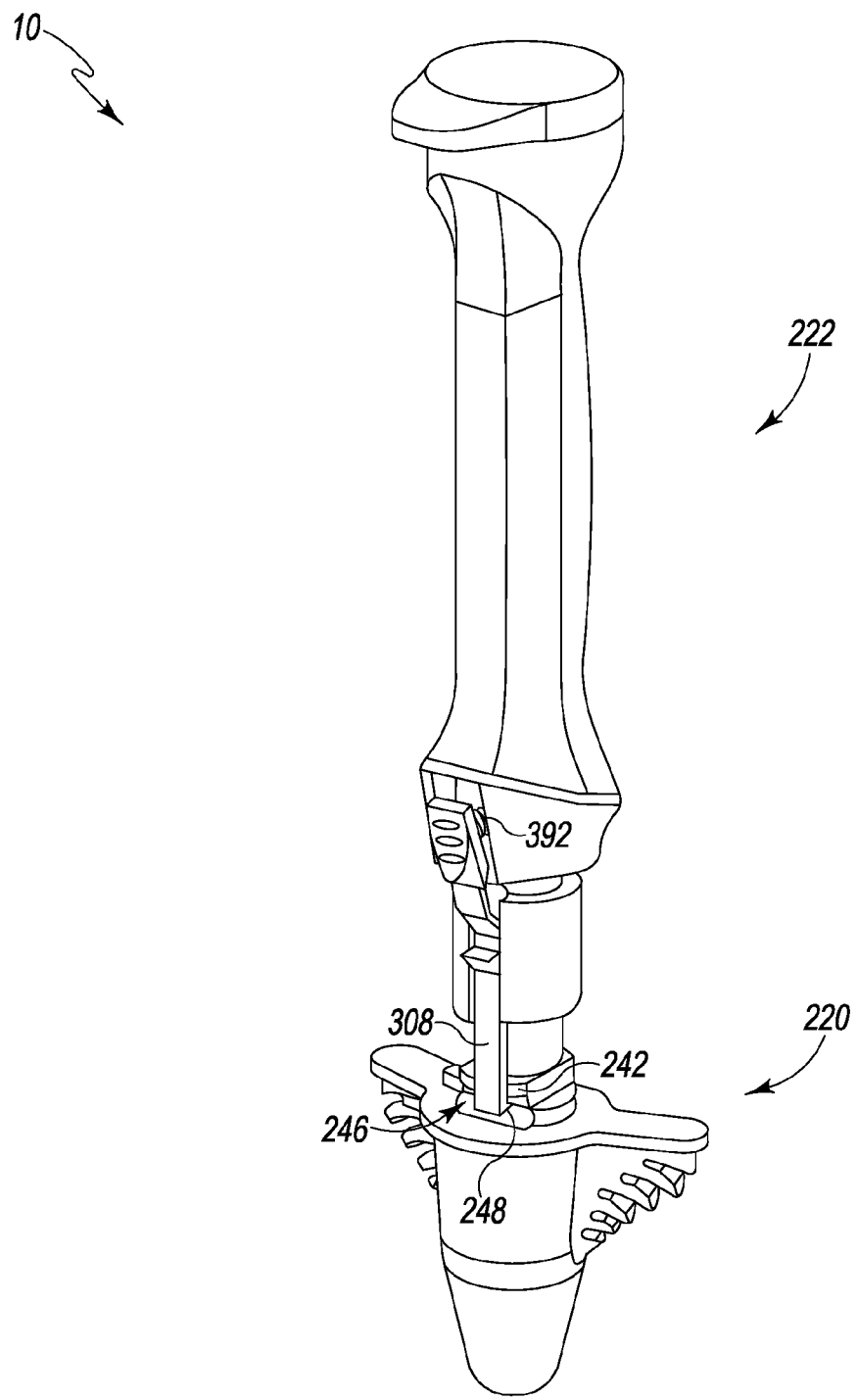

Once the keel punch 220 is selected, the surgeon attaches the keel punch 220 to the impaction handle 222, as shown in FIG. 17. As described above, the surgeon positions the guide pin 268 of the impaction handle 222 in the opening 262 of the keel punch 220 and presses on the user-operated button 348 of the lever 308 with a predetermined amount of force to overcome the bias exerted by the spring 392, thereby causing the lever 308 to pivot about the joint 366. As the lever 308 is pivoted, the locking flange 248 is moved away from the flat face 384 of the guide pin 268, and the guide pin 268 may be advanced along the passageway 266 defined in the keel punch 220 until the post 236 of the keel punch 220 is placed in contact with the end face 382 of the rod 380. In that position, the locking flange 248 is positioned over the lever-receiving notch 246. When the surgeon releases the button 348, the spring 392 urges the lever 308 to pivot about the joint 366 and the locking flange 248 is advanced into the notch 246, thereby securing the keel punch 220 to the impaction handle 222.

Figure 18:
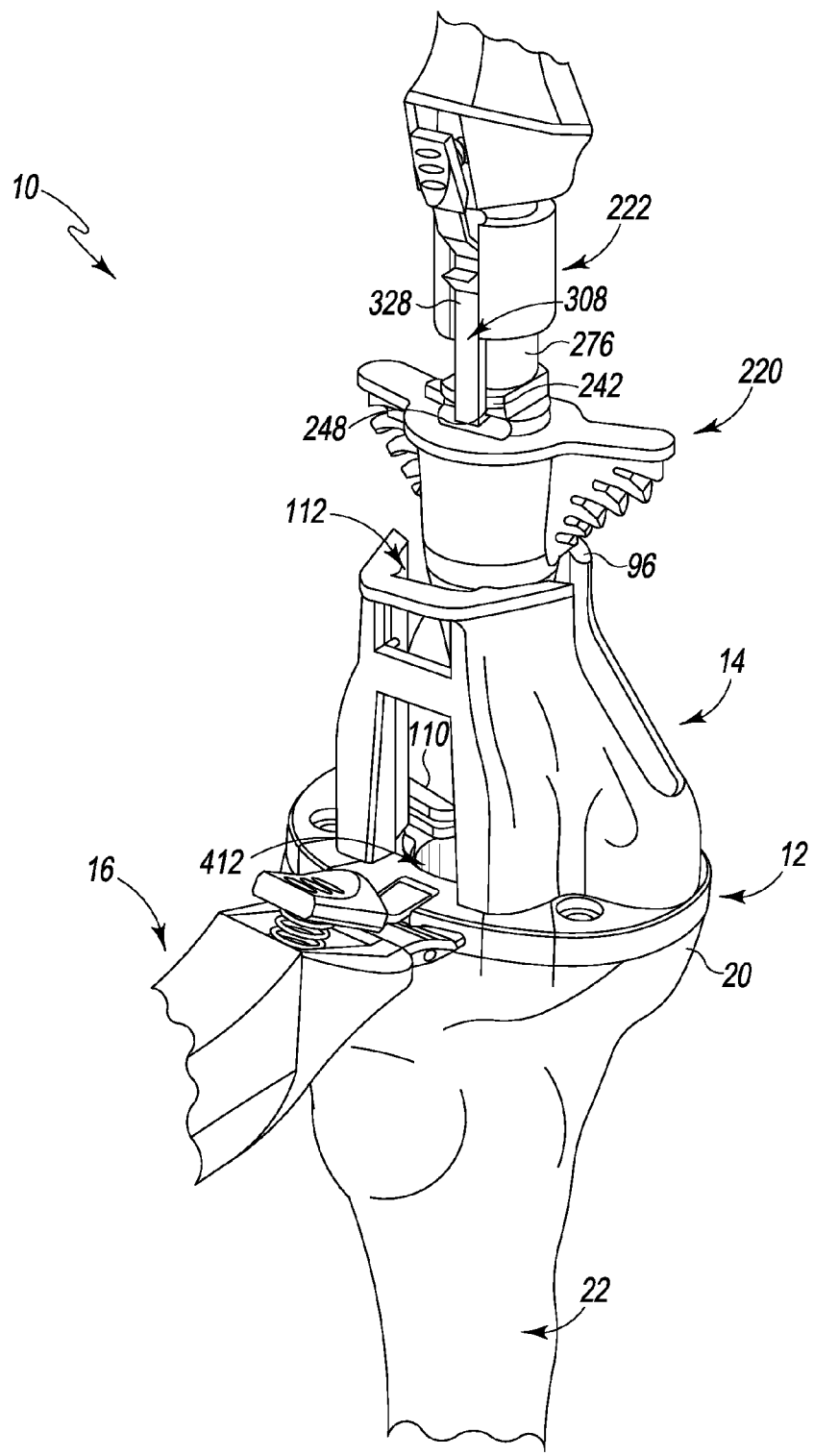
Figure 19:
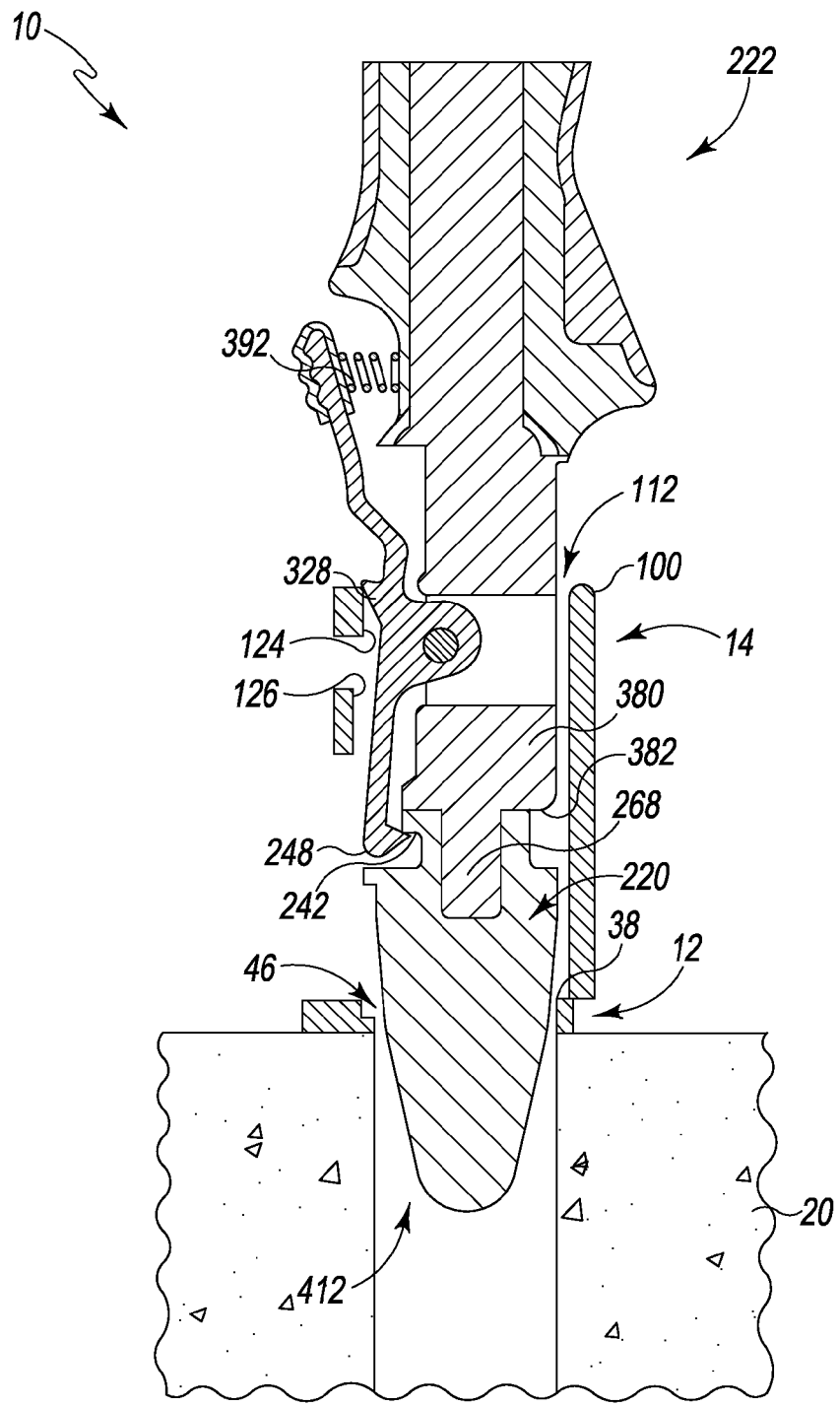

In block 512 of the procedure 500, the surgeon inserts the keel punch 220 and the attachment end 276 of the impaction handle 222 into the upper guide opening 96 of the guide tower 14. As shown in FIG. 18, the keel punch 220 and the impaction handle 222 are advanced through the upper guide opening 96 and along the passageway 112. As shown in FIG. 19, the catch 328 of the lever 308 is advanced into contact with the upper surface 100 of the tower base 80. As the surgeon pushes the impaction handle 222 deeper into the guide tower 14, the catch 328 advances along the interior surface 124 of the inner wall 126 of the guide tower 14 and the keel punch 220 passes through the plate opening 38 of the tibial base trial 12 into the proximal end 20 of the patient's tibia 22.

Figure 20:
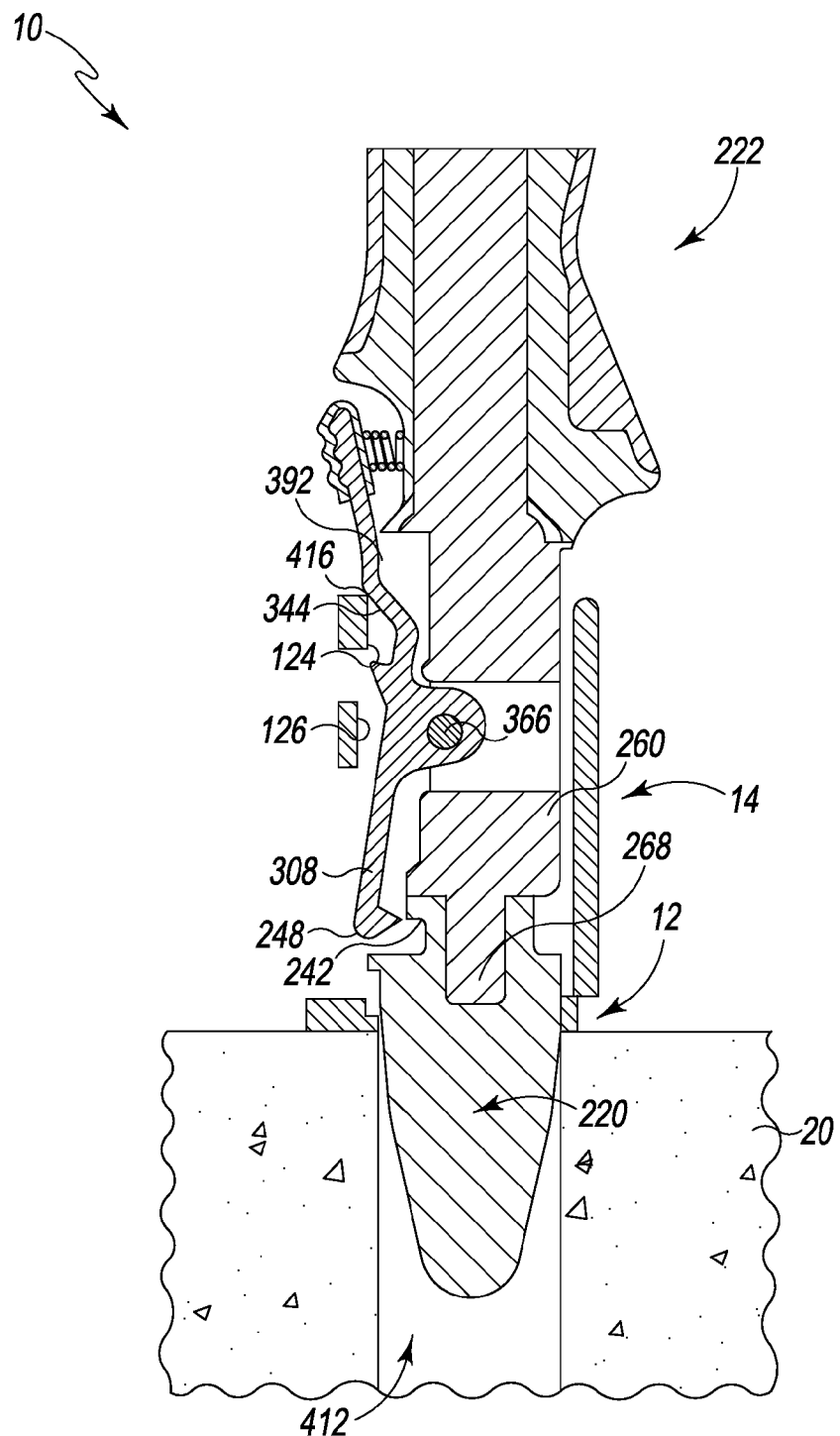

In block 514 of the procedure 500, the surgeon impacts the keel punch 220 into the patient's tibia 22 to seat the keel punch 220 therein. To do so, the surgeon may strike the head 288 of the impaction handle 222 with a mallet or other instrument to drive the keel punch 220 into the patient's tibia 22. The teeth 260 defined in the lower arms 252 of the keel punch 220 engage the patient's tibia 22 and enlarge the drilled-hole 412 into an opening 404 sized to receive a tibial implant. As shown in FIG. 20, the inclined top surface 344 of the actuation arm 312 is moved into contact with the upper edge 416 of the interior surface 124 of the inner wall 126 of the guide tower 14 as the keel punch 220 is driven into the patient's tibia 22. Contact between the interior surface 124 of the guide tower 14 and the inclined top surface 344 of the lever 308 exerts the predetermined amount of force on the lever 308 to overcome the bias exerted by the spring 392. When the spring bias is overcome, the lever 308 pivots about the joint 366, thereby moving the locking flange 248 away from the lip 242 of the keel punch 220. In that way, the lever 308 is actuated automatically by the contact between the impaction handle 222 and the guide tower 14.

Figure 21:
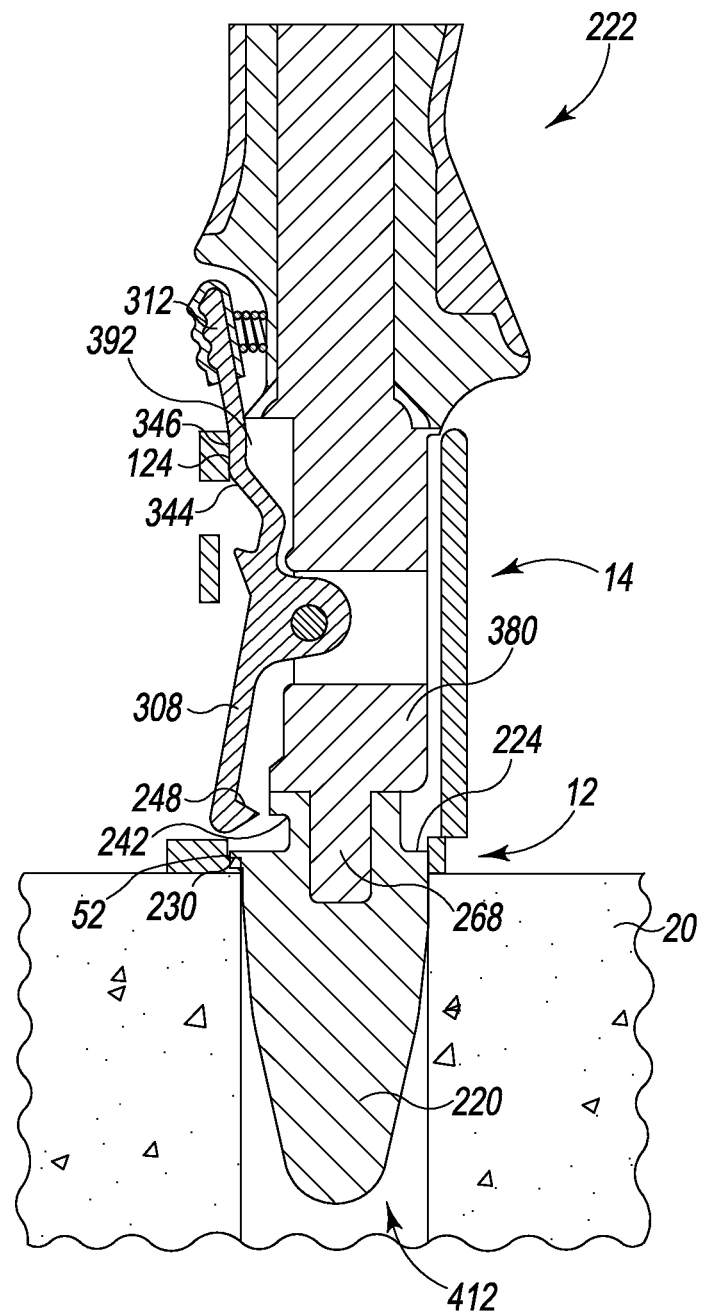
Figure 22:
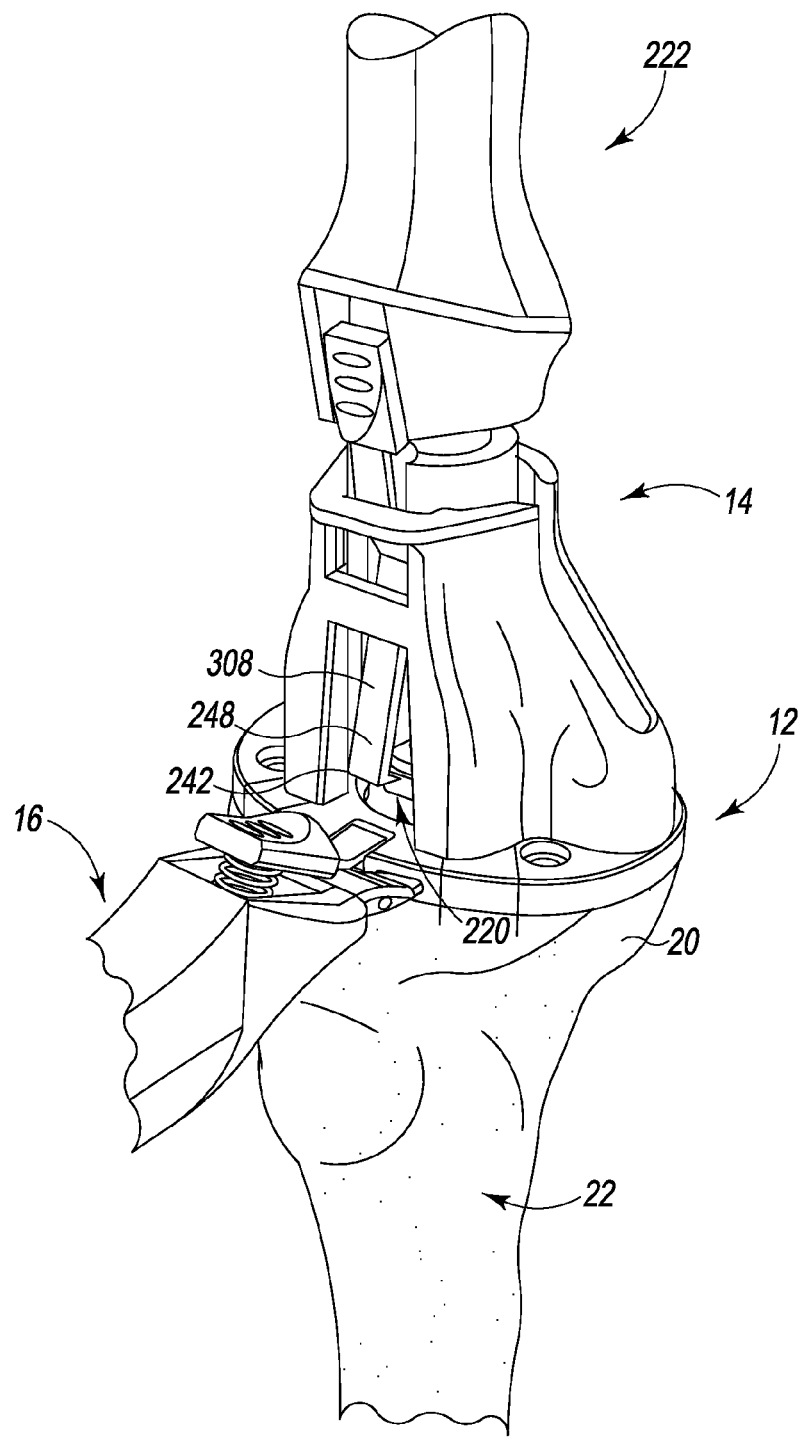
Figure 23:
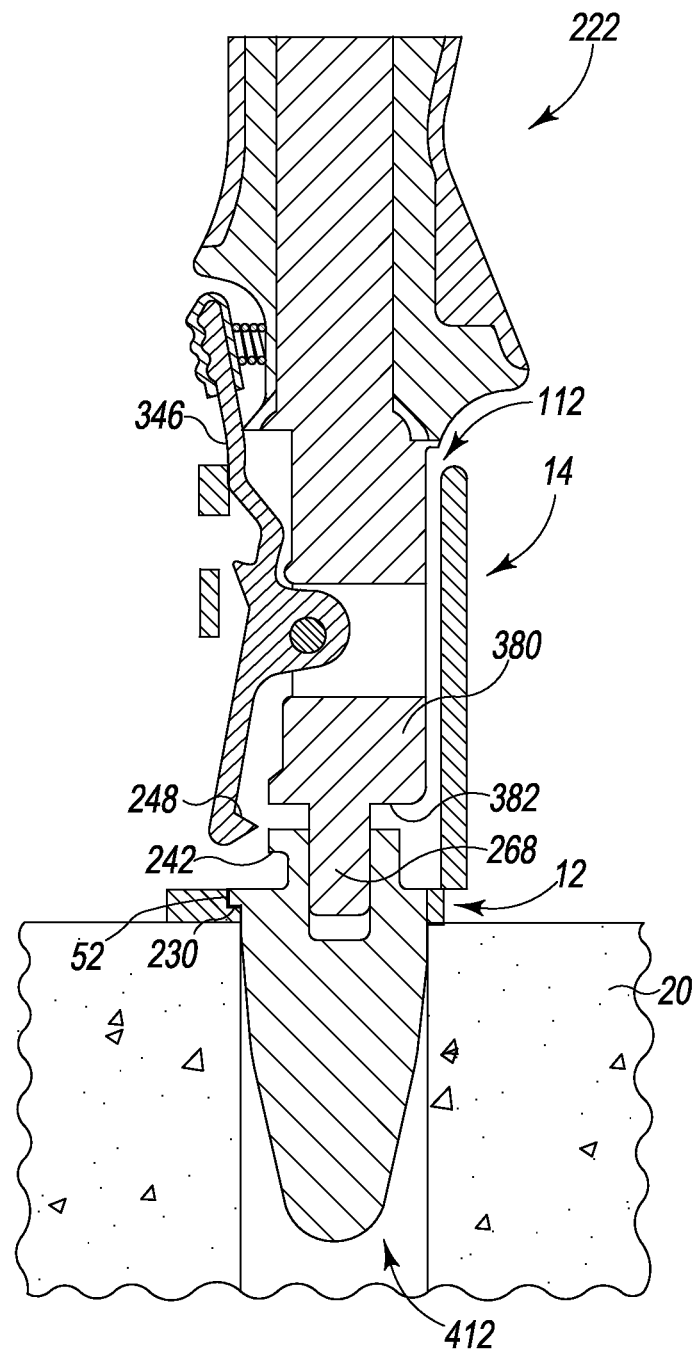

The surgeon continues driving the keel punch 220 into the patient's tibia 22 until the keel punch 220 is properly seated therein. As the keel punch 220 is driven deeper into the patient's tibia 22, the actuation arm 312 of the lever 308 is advanced along the interior surface 124 of the guide tower 14 and the inclined top surface 346 of the actuation arm 312 is brought into contact with the interior surface 124. As shown in FIG. 21, contact between the inclined top surface 346 and the interior surface 124 causes the lever 308 to pivot further about the joint 366, thereby completely removing the locking flange 248 from engagement with the lip 242 of the keel punch 220. When the keel punch 220 is seated, the bottom surface 230 of the upper frame 224 of the punch 220 engages the shelf surface 52 of the base trial 12, as shown in FIGS. 21 and 22.

In the next block 516 of the procedure 500, the surgeon removes the impaction handle 222 from the seated keel punch 220. To do so, as shown FIG. 23, the surgeon pulls the handle 222 upward along the passageway 112 of the guide tower 14. Because the actuation arm 312 remains in contact with the interior surface 124 of the tower 14, the locking flange 248 is spaced apart from the lip 242 and remains detached from the keel punch 220. As such, the keel punch 220 remains seated in the patient's tibia 22 as the impaction handle 222 moves up the passageway 112.

Figure 24:
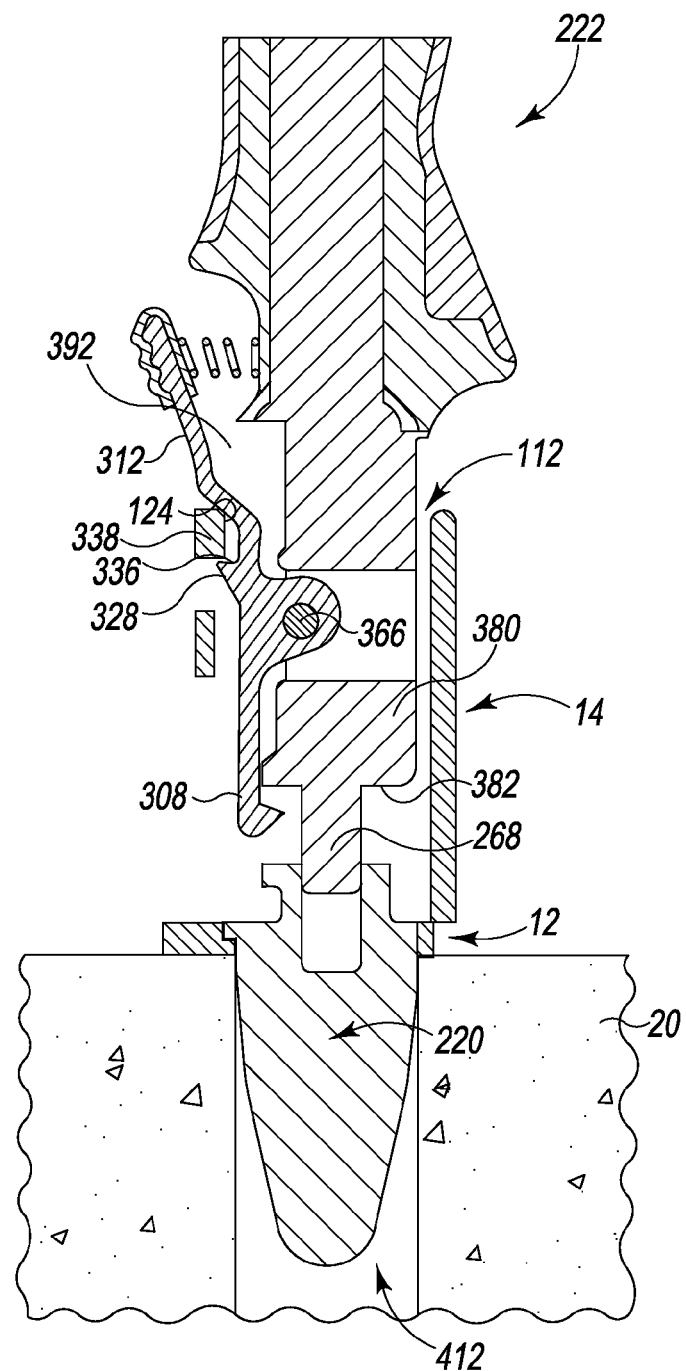

In the next block 518 of the procedure 500, the impaction handle 222 is attached to the guide tower 14. To do so, the surgeon merely continues pulling the impaction handle 222 upward along the passageway 112, and the lever 308 is actuated automatically to attach the impaction handle 222 to the guide tower 14. As shown in FIG. 24, the actuation arm 312 of the lever 308 is withdrawn from the passageway 112 of the guide tower 14 as the impaction handle 222 moves up the passageway 112. When the actuation arm 312 moves out of contact with the interior surface 124 of the guide tower 14, the spring 392 urges the lever 308 to pivot about the joint 366 and moves the lever 308 back into contact with the rod 380. In that way, the lever 308 is actuated automatically. Additionally, as shown in FIG. 24, the rear face 336 of the catch 328 of the impaction handle 222 engages the upper sidewall 338 of the guide tower 14, thereby securing the guide tower 14 to the impaction handle 222.

Figure 25:
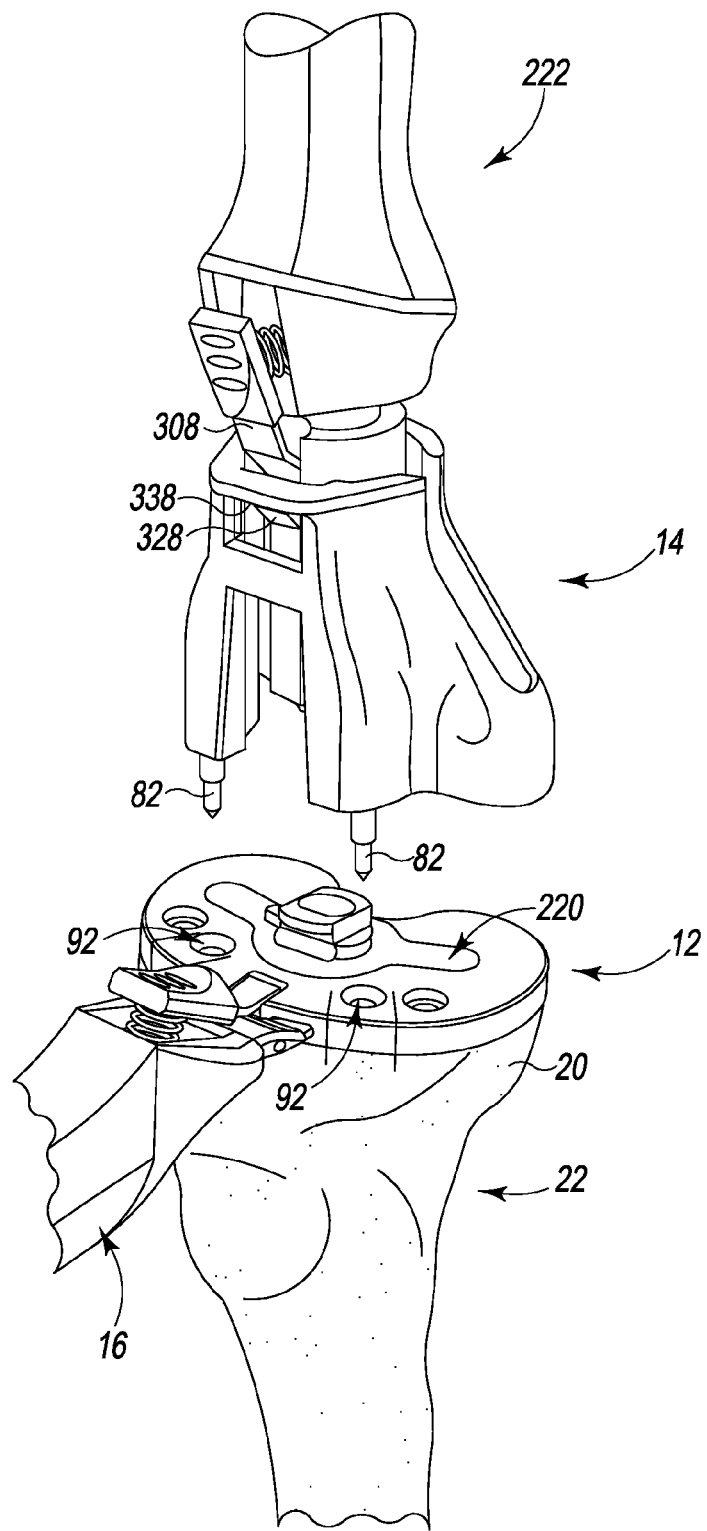

In block 520 of the procedure 500, the surgeon uses the impaction handle 222 to remove the guide tower 14 from the base trial 12. To do so, the surgeon continues to pull upward on the impaction handle 222. Because the catch 328 is engaged with the upper sidewall 338 of the guide tower 14, the guide tower 14 is pulled upward along with the impaction handle 222. As shown in FIG. 25, the fixation pins 82 are withdrawn from the patient's tibia 22 as the guide tower 14 is removed from the base trial 12, leaving only the tibial base trial 12 positioned on the proximal end 20 of the patient's tibia 22 and the keel punch 220 seated therein. The base trial 12 and the keel punch 220 may be used to perform additional selection and evaluation of surgical implants before being removed from the patient's tibia 22.

After the guide tower 14 is removed from the base trial 12, the impaction handle 222 may be removed from the guide tower 14 by actuating the lever 308. The surgeon merely presses on the user-operated button 348 of the lever 308 with a predetermined amount of force to overcome the bias exerted by the spring 392, thereby causing the lever 308 to pivot about the joint 366. As the lever 308 is pivoted, the catch 328 is disengaged from the upper sidewall 338 of the guide tower 14, thereby permitting the surgeon to separate the handle 222 from the guide tower 14.

Figure 26:
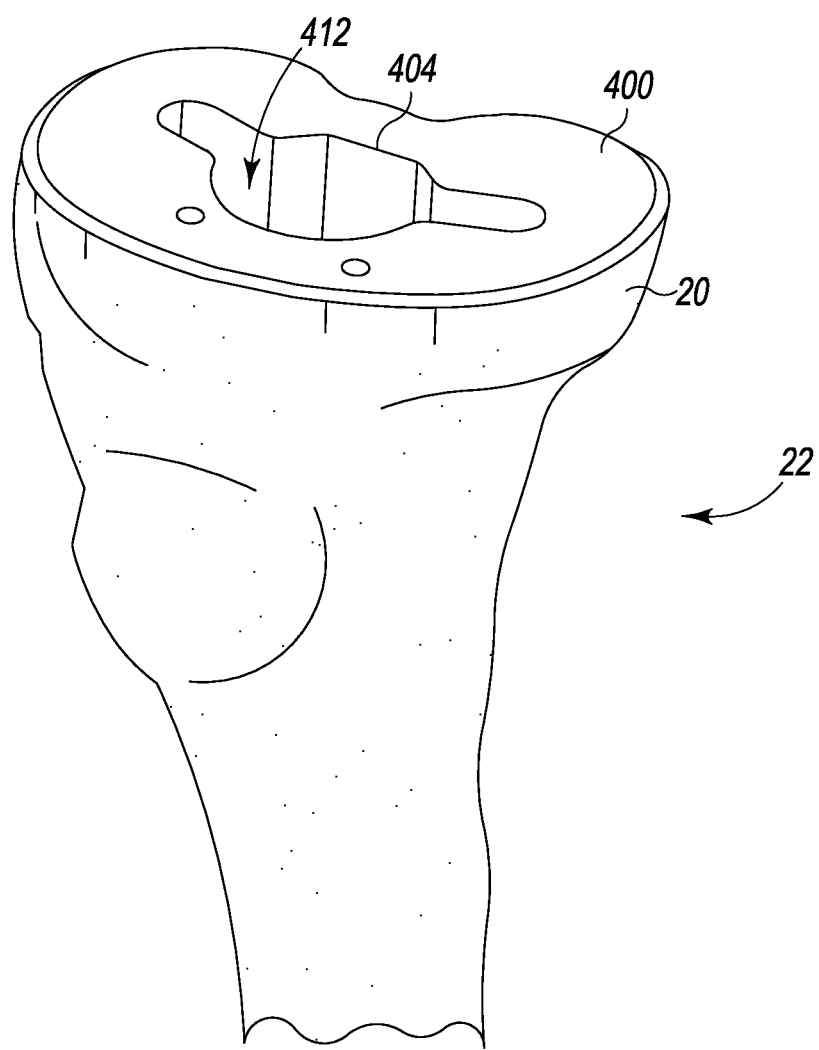
FIG. 26 is a perspective view of the resected surface of the proximal end of the patient's tibia subsequent to the performance of the procedure of FIG. 11.

As shown in FIG. 26, the resultant features formed in the proximal end 20 of the patient's tibia 22 are configured to receive a tibial implant. It should be appreciated that the tibial implant may be press fit into the tibia 22 or, alternatively, may be secured to the tibia 22 by use of bone cement.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument assembly comprising:
 a base trial adapted to be positioned on a proximal end of a patient's resected tibia, the base trial including a plate having (i) an opening defined therein, and (ii) a pair of fixation pin holes defined in an anterior aspect, and
 a guide tower including (i) a tower base adapted to be positioned on the base trial, the tower base having a passageway defined therein that is configured to be substantially aligned with the opening of the plate when the tower base is positioned on the base trial, and (ii) a pair of fixation pins, each of the fixation pins extending downwardly from an end secured to an anterior aspect of the bottom surface of the tower base to a tip, and each of the fixation pins being sized to be received in and extend outwardly from each of the fixation pin holes of the base trial when the tower base is positioned on the base trial.

2. The orthopaedic surgical instrument assembly of claim 1, further comprising a second pair of fixation pins, wherein the plate of the base trial has a second pair of fixation pin holes defined in the anterior aspect and each of the second pair of fixation pins is sized to be received in and extend outwardly from each of the second pair of fixation pin holes.

3. The orthopaedic surgical instrument assembly of claim 1, further comprising a handle removably coupled to the anterior aspect of the plate.

4. The orthopaedic surgical instrument assembly of claim 3, wherein:
 the plate has a notch defined therein and a pair of apertures defined on each side of the notch,
 the handle includes a body, a pair of tabs extending from the body that are sized to be received in the pair of apertures, and a lever arm pivotally coupled to the body, the lever arm having a flange and being movable between (i) a first position in which the flange is received in the notch defined in the plate such that the handle is secured to the base trial, and (ii) a second position in which the flange is spaced apart from the notch such that the handle may be removed from the base trial.

5. The orthopaedic surgical instrument assembly of claim 4, further comprising a biasing member that biases the lever arm in the first position.

6. The orthopaedic surgical instrument assembly of claim 1, wherein the opening of the base trial and the passageway of the guide tower are sized to receive a surgical drill.

7. The orthopaedic surgical instrument assembly of claim 6, further comprising a drill stop adapted to be positioned at an upper end of the guide tower.

8. The orthopaedic surgical instrument assembly of claim 7, wherein the drill stop is formed from a first material and the guide tower is formed from a second material different from the first material.

9. The orthopaedic surgical instrument assembly of claim 1, wherein the plate has a plurality of alignment etchings defined in the anterior aspect to align the plate with the proximal end of the patient's resected tibia.

10. An orthopaedic surgical instrument assembly comprising:
 a base trial adapted to be positioned on a proximal end of a patient's resected tibia, the base trial including a plate having an opening defined therein, and
 a guide tower including a tower base adapted to be positioned on the base trial, the tower base having (i) an anterior surface, (ii) an inner surface defining a passageway that is configured to be substantially aligned with the opening of the plate when the tower base is positioned on the base trial, (iii) a first aperture extending inwardly from the anterior surface to the inner surface such that the first aperture is in communication with the passageway, and (iv) a second aperture extending inwardly from the anterior surface to the inner surface such that the second aperture is in communication with the passageway, the second aperture being positioned above the first aperture.

11. The orthopaedic surgical instrument assembly of claim 10, wherein the plate has a plurality of fixation pin holes defined in an anterior aspect thereof.

12. The orthopaedic surgical instrument assembly of claim 10, wherein the tower base of the guide tower includes a pair of fixation pins extending downwardly from an anterior aspect of the tower base, each of the fixation pins being sized to be received in and extend outwardly from one of the fixation pin holes of the base trial when the tower base is positioned on the base trial.

13. The orthopaedic surgical instrument assembly of claim 10, further comprising a surgical drill, wherein the opening of the base trial and the passageway of the guide tower are sized to receive the surgical drill.

14. The orthopaedic surgical instrument assembly of claim 13, wherein the surgical drill has a plurality of horizontal lines defined thereon, and the guide tower extends a predetermined height corresponding to a first horizontal line of the plurality of horizontal lines and a first predetermined drilled-hole depth in the patient's tibia.

15. The orthopaedic surgical instrument assembly of claim 14, further comprising a drill stop adapted to be positioned at an upper end of the guide tower, wherein the drill stop and the guide tower extend a second predetermined height corresponding to a second horizontal line of the plurality of horizontal lines and a second predetermined drilled-hole depth in the patient's tibia.

16. An orthopaedic surgical instrument assembly comprising:
   a guide tower for a surgical drill, the guide tower comprising:
   a tower base including (i) an anterior aspect having an anterior surface, (ii) an inner surface defining a vertically-extending passageway, (iii) a first aperture, the first aperture extending orthogonally relative to the passageway from the anterior surface to the inner surface such that the first aperture is in communication with the passageway, and (iv) a second aperture positioned above the first aperture, the second aperture extending orthogonally relative to the passageway from the anterior surface to the inner surface such that the second aperture is in communication with the passageway; and
   a pair of fixation pins extending downwardly from the anterior aspect of the tower base, each fixation pin being configured to be inserted into a proximal end of a patient's resected tibia.

17. The orthopaedic surgical instrument assembly of claim 16, wherein the inner surface defines a circular opening in an upper end of the tower base and the passageway extends downwardly from the circular opening.

18. The orthopaedic surgical instrument assembly of claim 17, wherein the inner surface further defines a pair of slots connected to the circular opening.

19. The orthopaedic surgical instrument assembly of claim 16, further comprising a drill stop adapted to be positioned at an upper end of the guide tower.

20. The orthopaedic surgical instrument assembly of claim 16, wherein each fixation pin of the pair of fixation pins includes (i) a first section having a first cross-sectional diameter and (ii) a second section extending downwardly from the first section that has a second cross-sectional diameter, the second cross-sectional diameter being less than the first cross-sectional diameter.

* * * * *